(12) United States Patent
Qizilbash et al.

(10) Patent No.: US 9,919,016 B2
(45) Date of Patent: Mar. 20, 2018

(54) PRODUCT AND METHOD OF DEPLOYING KALE DERIVATIVES FOR ANTI-CANCER EFFECTS

(71) Applicants: Bilal Qizilbash, Flushing, NY (US); Elizabeth Brandon, Jackson, MS (US)

(72) Inventors: Bilal Qizilbash, Flushing, NY (US); Elizabeth Brandon, Jackson, MS (US)

(*) Notice: Subject to any disclaimer, the term of this patent is extended or adjusted under 35 U.S.C. 154(b) by 0 days.

(21) Appl. No.: 15/040,667

(22) Filed: Feb. 10, 2016

(65) Prior Publication Data
US 2016/0235799 A1 Aug. 18, 2016

Related U.S. Application Data

(60) Provisional application No. 62/114,440, filed on Feb. 10, 2015.

(51) Int. Cl.
*A61K 36/31* (2006.01)
*A61K 9/00* (2006.01)

(52) U.S. Cl.
CPC ............ *A61K 36/31* (2013.01); *A61K 9/0014* (2013.01); *A61K 9/0095* (2013.01)

(58) Field of Classification Search
CPC .......................... A61K 9/0014; A61K 9/0095
See application file for complete search history.

(56) References Cited

U.S. PATENT DOCUMENTS

| | | | |
|---|---|---|---|
| 6,262,284 B1 | 7/2001 | Khachik | |
| 6,387,434 B1 | 5/2002 | Takaoka | |
| 6,416,807 B1 | 7/2002 | Yamamoto | |
| 6,869,621 B2 | 3/2005 | Hwang et al. | |
| 6,909,021 B2 | 6/2005 | Crombie | |
| 8,124,135 B2 | 2/2012 | Pietrzkowski | |
| 2009/0306219 A1 | 12/2009 | Presti | |
| 2009/0324705 A1 | 12/2009 | Vikhrieva | |

FOREIGN PATENT DOCUMENTS

| | | | |
|---|---|---|---|
| JP | 2004091396 A | * | 3/2004 |
| WO | Wo-2013/062190 A1 | * | 5/2013 |
| WO | 201401729 A2 | | 1/2014 |
| WO | 2015163442 A1 | | 10/2015 |

OTHER PUBLICATIONS

By Bak et al., Cooking Process Decreased Nutraceutical Contents and in Vitro Anticancer Effects in Kale Juices, 2007, Cancer Prev Res, vol. 12, pp. 303-309.*
Olsen et al., Antiproliferative Effects of Fresh and Thermal Processed Green and Red Cultivars of Curly Kale (Brassica oleracea L. convar acephala var. sabellica, Jul. 6, 2012, Journal of Agricultural and Food Chemistry, vol. 60, pp. 7375-7383.*
Kanengiser, Kale Research Drives Mississippi College Graduate Student, May 9, 2014, University News.*
Pavlovic, Elizabeth Brandon, Bilal Qizilbash, Kale Research, Apr. 26, 2014, Real Responsible Eating and Living.*

* cited by examiner

*Primary Examiner* — Ali Soroush
(74) *Attorney, Agent, or Firm* — Carter, DeLuca, Farrell & Schmidt, LLP

(57) ABSTRACT

The present disclosure describes chemopreventative and/or chemotherapeutic compositions for inducing apoptosis in cancer cells which include kale and methods of inducing apoptosis in cancer cells utilizing the chemopreventative and/or chemotherapeutic compositions including kale.

14 Claims, 30 Drawing Sheets

COMPARISON OF WASHING METHODS OF COMMERCIAL KALE. BOTH KALE LEAVES WERE WASHED WITH EQUAL AMOUNTS OF WATER. THE LEAF ON THE LEFT WAS WASHED IN PLAIN TAP WATER AND THE LEAF ON THE RIGHT WAS WASHED WITH DAWN DISHWASHING SOAP.

| Source of Variation | Sum of Squares | df | Mean Squares | F | p |
|---|---|---|---|---|---|
| Between | 2.4554E+13 | 2 | 1.2277E+13 | 60.20 | 0.0001 |
| Error | 1.2236E+12 | 6 | 2.0393E+11 | | |
| total | 2.5778E+13 | 8 | | | |

ANOVA results for sonicated juiced kale extract and non-sonicated juiced kale treated melanoma cells.

Figure 3C

| Source of Variation | Sum of Squares | df | Mean Squares | F | p |
|---|---|---|---|---|---|
| Between | 4.4230E+09 | 2 | 2.2140E+09 | 28.89 | 0.0001 |
| Error | 6.1304E+08 | 8 | 7.6630E+07 | | |
| total | 5.0410E+09 | 10 | | | |

ANOVA results for heated juiced kale and non-heated juiced kale treated melanoma cells.

Figure 7B

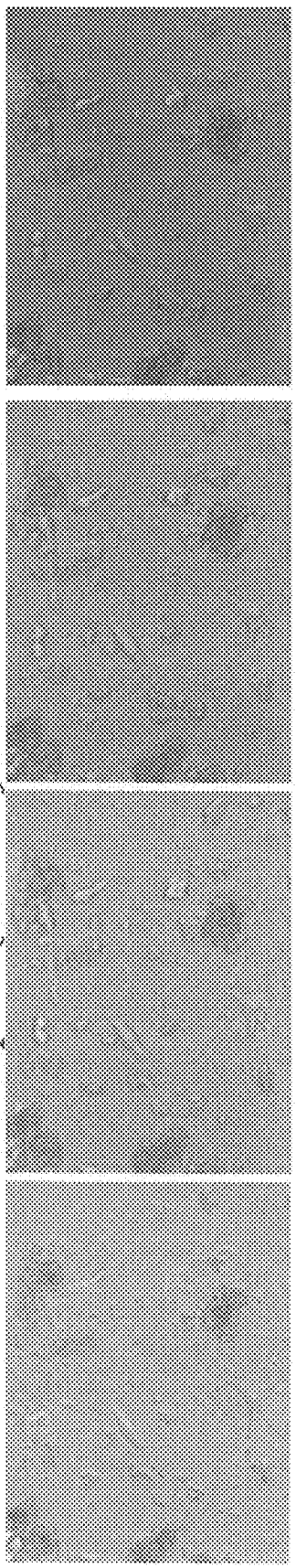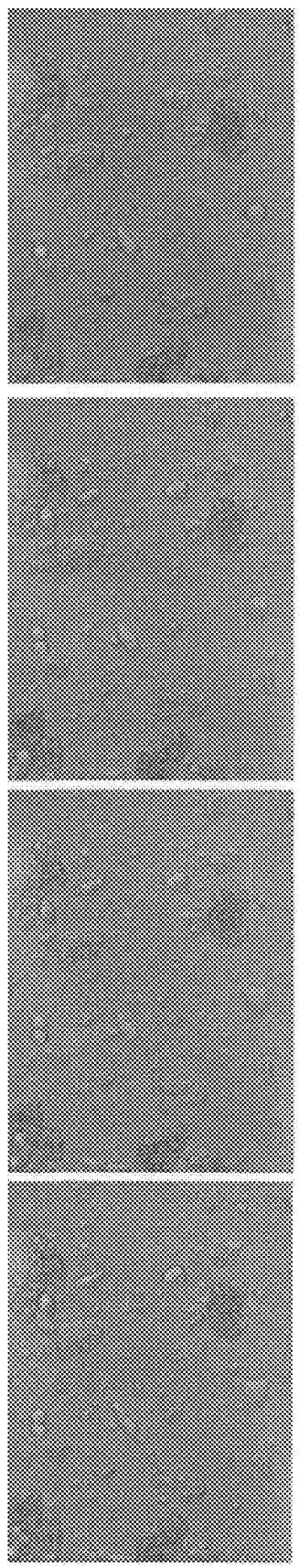
Kale Video Time Lapse (hours)
Time 0
Figure 11A
Time 2
Figure 11B
Time 4
Figure 11C
Time 6
Figure 11D
Time 8
Figure 11E
Time 10
Figure 11F
Time 12
Figure 11G
Time 14
Figure 11H Time 0 hour

| Source of Variation | Sum of Squares | d.f. | Mean Squares | F | p |
|---|---|---|---|---|---|
| Between | 1.2770E+09 | 2 | 6.3848E+08 | 44.87 | 0.001 |
| Error | 1.2863E+08 | 9 | 1.4292E+07 | | |
| total | 1.4056E+09 | 11 | | | |

Figure 12B

ANOVA results for sonicated juiced kale extract and non-sonicated juiced kale treated epithelial cells at 100 hours.

| Treatment | Melanoma | Epithelial | Fibroblasts |
|---|---|---|---|
| Juiced Kale | Cell Death | No Death | No Death |
| Sonicated juiced kale extract | Cell Death | Cell Death | No Death |
| Heated juiced kale | No Death | Not Tested | Not Tested |
| Green Lettuce Juice | No Death | Not Tested | No Death |

Figure 15

PRODUCT AND METHOD OF DEPLOYING KALE DERIVATIVES FOR ANTI-CANCER EFFECTS

CROSS-REFERENCE TO RELATED APPLICATION

The present application claims the benefit of and priority to U.S. Provisional Application Ser. No. 62/114,440, filed on Feb. 10, 2015, the entire disclosure of which is incorporated herein by reference.

BACKGROUND

Technical Field

The present disclosure relates to products and methods including kale as a cancer chemopreventative and/or chemotherapeutic agent. More particularly, the present disclosure relates to chemopreventative and/or chemotherapeutic compositions which include juiced kale, which is capable of killing and/or inducing apoptosis of hyperproliferative cells, including cancerous and precancerous cells.

Background of Related Art

The war on cancer, which began in 1971, continues with few drugs that selectively kill tumor cells despite the wide array of molecular targets. Tumor cells' astounding adaptability explains much of the poor performance of some of the current therapies. Drugs designed to inactivate certain receptor tyrosine kinases have a brief success that is usually followed by the development of drug resistance. Similarly, drugs designed to induce enough DNA damage to trigger apoptosis are effective until the genes encoding signaling proteins required for cell death become silenced or mutated. Multi-drug resistance can also occur if tumor cells increase their expression of certain ABC transporters in the plasma membrane. Genetically engineered viruses for virotherapy and tumor vaccines designed to enable MHC class I molecules to present tumor antigens to immune cells have shown efficacy in animal studies, yet few such therapies have been tested in humans in large numbers. Drug cocktails are more effective, but may worsen side effects and the composition must be adjusted to stay ahead of drug resistance. Adaptation is an emergent property of the cooperation among heterogeneous tumor cells and between tumor cells and stromal cells. The battle raging between clinicians and tumor cells is an arms race with escalating costs and proportionally small decreases in human suffering.

Humans have been gathering and archiving knowledge of medicinal plants for tens of thousands of years. Natural products research provides society with untold numbers of life saving drugs. Several chemotherapies have been developed from plants, e.g. paclitaxel, vincristine, and irinotecan. The treatment of many cellular disorders, for example, tumors, and other hyperproliferative diseases, may involve the systemic use of therapeutic agents. These agents may exert their activity in a variety of ways. In many, if not most instances, the therapeutic agent may not address the abnormal cell specifically, but rather tends to exert its effectiveness systemically across all cells. Systemic administration may therefore expose both abnormal cells and healthy, normal cells to the effects of the therapeutic agent. Although potentially effective therapeutically against the abnormal cells, systemic administration of the therapeutic effect may be detrimental or cause detrimental side effects to the normal healthy cells. This may result in a smaller amount of the intended dosage of the therapeutic agent reaching and addressing the abnormal cells or tumor. In addition, a greater amount of the intended dosage of the therapeutic agent may reach and address the normal healthy cells. Systemic delivery of therapeutic agents may hinder the dosing parameters from being maximized because of the potentially harmful side effects. In addition, the detrimental effect to the normal healthy cells may weaken and/or cause a decrease in population numbers of the healthy cells thereby decreasing the ability of the healthy cells to fight the proliferation of the abnormal cells.

For example, anti-neoplastic agents may be cytotoxic. The anti-neoplastic agents may exert their cytotoxic activity in a variety of ways, sometimes interfering with a cellular function essential for the replication and/or viability of the cell. Many anti-neoplastic agents may be administered systemically and may not be designed specifically to attack the abnormal cells only, but rather may be designed to exert their effectiveness due to the more rapid proliferation of the abnormal cell, as compared to normal healthy cells. While many organs of the body of a mammalian host regenerate cells rather slowly, there may also be other organs, particularly bone marrow, which involve rapid proliferation of stem cells. Therefore, anti-neoplastic agents may not only affect the slowly regenerating cells detrimentally, but may also have a particularly pernicious effect on bone marrow production and the immune system.

Despite the possible disadvantages and side effects of employing the systemic use of therapeutic agents, this method has found extensive application because the agents may have provided some positive results. However, there remains a substantial interest in being able to employ therapeutic agents in a manner which is less systemic, i.e., directed more specifically toward the abnormal cells, while simultaneously protecting sensitive normal cells, in the vicinity of and distant from the site of the abnormal cells. In addition, there remains a need for therapeutic compositions which are directed more specifically toward the abnormal cells while simultaneously promoting proliferation of the normal healthy cells, in the vicinity of and/or distant from the site of abnormal cells.

SUMMARY

The present disclosure provides chemopreventative and/or chemotherapeutic compositions suitable for killing and/or inducing apoptosis in precancerous and/or cancer cells, which include kale and/or in particular embodiments juiced kale. In some embodiments, the compositions may include only juiced kale. In some embodiments, the compositions may further include at least one of a pharmaceutically acceptable carrier and/or a surfactant. In some embodiments, the pharmaceutically acceptable carrier may be water, dextrose, or saline. In some embodiments, the compositions may further include at least one therapeutic agent and/or optional ingredients.

The chemopreventative and/or chemotherapeutic compositions may be utilized in any common pharmaceutical formulation suitable for the delivery of the kale, and/or particularly juiced kale. Some non-limiting formulations include solutions, suspension, or powders suitable for topical delivery, oral ingestion, inhalation, and injectable delivery.

The chemopreventative and/or chemotherapeutic compositions are suitable for killing and/or inducing apoptosis in a variety of precancerous and cancerous cells. In particular embodiments, the compositions are suitable for killing and/or inducing apoptosis in melanoma cells, basal cell carcinomas, and skin tags.

In addition to killing and/or inducing apoptosis of precancerous and cancerous cells, the chemopreventative and/or chemotherapeutic compositions may also be applied and/or be exposed to healthy cells, i.e., non-precancerous or non-cancerous cells, wherein the compositions are non-toxic and/or not detrimental to the healthy cells. In yet other embodiments, the compositions may further promote proliferation and/or growth of the healthy cells, i.e., non-precancerous or non-cancerous cells while simultaneously killing and/or inducing apoptosis of the non-healthy cells.

Methods of killing and/or inducing apoptosis in non-healthy cells, i.e., precancerous and/or cancerous cells, are also described. In embodiments the chemopreventative and/or chemotherapeutic compositions described herein including the kale is applied to the cancer cells. In some embodiments, the non-healthy cells are on the surface of a tissue and the composition is a topical solution or suspension that can be applied directly to the non-healthy cells.

In other embodiments, methods of reducing cancerous or precancerous cells are described wherein the chemopreventative and/or chemotherapeutic compositions including the kale may be in a form suitable for oral-ingestion to produce systemic effects. The cells may be skin lesions, such as basal cell carcinoma or skin tags, wherein oral-ingestion provides a more systemic distribution of the composition, while maintain the ability to reduce, shrink, and/or remove the skin lesions. In embodiments, the composition may be utilized in both a topical manner and an orally-ingested form.

BRIEF DESCRIPTION OF THE DRAWINGS

The accompanying drawings, which are incorporated in and constitute a part of the present disclosure, illustrate embodiments of the disclosure and, together with a general description given herein, and the detailed description of the embodiments provided herein, serve to explain the principles of the present disclosure.

FIG. 3C is a chart depicting ANOVA results for the sonicated juiced kale and the unfiltered juiced kale.

FIG. 7B is a chart depicting ANOVA results for the heated juiced kale and the non-heated unfiltered juiced kale.

FIG. 12B is a chart depicting ANOVA results for sonicated juiced kale and unfiltered juiced kale.

FIG. 15 is a chart summarizing the effects of various kale juice treatments.

DETAILED DESCRIPTION

Figure 1:
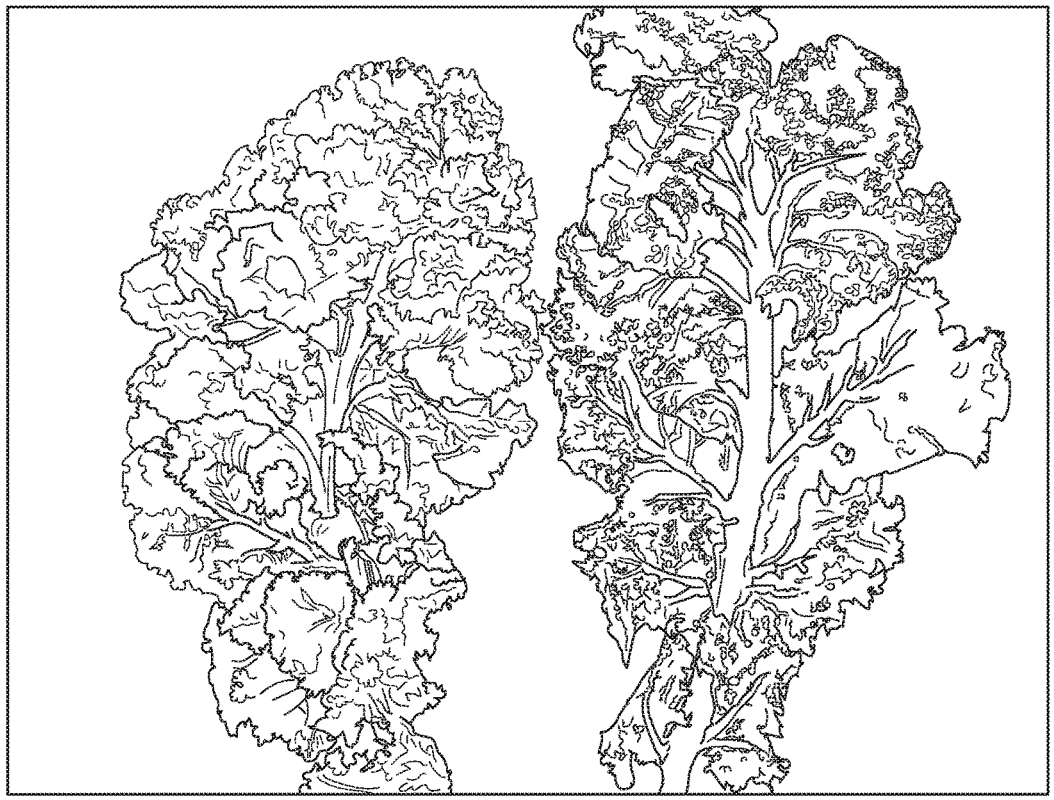
FIG. 1 is a photographic image from a top view of clean kale leaves, as described in at least one embodiment of the present application.

In the interest of brevity, reference made to chemopreventative compositions throughout the present disclosure is intended to encompass compositions which are chemopreventative and/or compositions which are chemotherapeutic.

Chemopreventative compositions and methods are provided herein for the treatment of hyperproliferative diseases including, but not limited to cancers, abnormal cellular growths, psoriasis, and the like. Hyperproliferative growth may include neoplastic or preneoplastic lesions or conditions such as psoriasis, keloids, nodules, or warts. It will be understood that the terms neoplastic and preneoplastic lesions may refer to any new or abnormal growth or cancer, such as: oncogenically transformed cells, carcinomas, melanomas, lymphomas, neuromas, spiromas, fibromas, blastomas, chodromas, gliomas, myxomas, thecomas, myelomas, both benign and malignant tumors, and sarcomas. Some non-limiting examples of cancers which may be treated with the chemopreventative compositions described herein include brain cancer, bone cancer, bladder cancer, breast cancer, pancreatic cancer, testicular cancer, spinal cancer, skin cancer, prostate cancer, colon cancer, lung cancer, thyroid cancer, and the like.

In embodiments, the chemopreventative compositions described herein are suitable for treating melanoma. In embodiments, the chemopreventative compositions described herein induce apoptosis of cancer cells, and particularly apoptosis of melanoma cells. In embodiments, the chemopreventative compositions described herein are suitable for treating basal cell carcinoma. In embodiments, the chemopreventative compositions are suitable for treating skin tags.

The chemopreventative compositions described herein include kale. Kale is a vegetable within the plant species *Brassica oleracea*. Some non-limiting examples of kale include curly-leaf kale, plain-leaf kale, rape leaf kale, leaf and spear kale, bumpy-leaf kale, baby kale, and ornamental kale. In embodiments, the chemopreventative compositions include kale derived from curly-leaf kale or baby kale.

In embodiments, the kale may be grown organically. In embodiments, the kale may be grown with the use of pesticides, herbicides, and/or insecticides. In embodiments, the kale may be grown without the use of pesticides, herbicides, and/or insecticides. In embodiments, the kale may be commercially available and not grown organically.

The chemopreventative compositions described herein may include kale in a derivatized and/or processed form. For example, in embodiments, the chemopreventative compositions may include juiced kale, i.e., kale juice. By "juiced," "juicing," and/or "juice," the whole kale leaf is processed to reduce the kale leaf to an average particle size having a mean diameter ranging from about 0.1 microns to about 500 microns. In embodiments, the juiced kale may include an average particle size having a mean diameter ranging from about 1 micron to about 300 microns. In still other embodiments, the juiced kale may include an average particle size having a mean diameter ranging from about 5 microns to about 250 microns. In still other embodiments, the juiced kale may include an average particle size having a mean diameter ranging from about 10 microns to about 150 microns. In still other embodiments, the juiced kale may include an average particle size having a mean diameter ranging from about 15 microns to about 100 microns. In still other embodiments, the juiced kale may include an average particle size having a mean diameter ranging from about 20 microns to about 75 microns.

In embodiments, the kale is juiced using a juicer, such as an electric juicer. In addition to having a reduced particle size, the juiced kale will include a reduced amount of non-soluble fiber commonly found in whole kale leaves prior to juicing. In embodiments, the juiced kale may include less than about 50% of the non-soluble fiber commonly found in whole kale leaves prior to juicing. In embodiments, the juiced kale may include less than about 55%, about 60%, about 65%, about 70%, about 75%, about 80%, about 85%, about 90%, about 95%, or about 100% of the non-soluble fiber commonly found in whole kale leaves prior to juicing.

In some embodiments, the chemopreventative compositions described herein may include kale which is blended. By "blended," "blending," and/or "blend," the kale is processed using a blender or mixer to chop the whole kale leaf into smaller pieces which can be seen with the naked eye with an average particle size having a mean diameter ranging from at least 0.75 mm or larger. In embodiments, the blended kale may include an average particle size having a mean diameter of at least 1 mm or larger. In still other embodiments, the blended kale may include an average particle size having a mean diameter of at least 1.5 mm. In embodiments, the kale may blended and/or further processed to produce a smaller average particle size however such a process may include or produce the kale to be heated.

In embodiments, the blended kale may be further processed via centrifugation to further reduce the mean diameter of the average particle size of the kale.

In still other embodiments, the chemopreventative compositions may include kale juice which is sonicated and/or filter sterilized. In embodiments, the kale juice may be unfiltered. In embodiments, the kale may be non-sterile. In embodiments, the kale juice may be raw. In embodiments, the kale juice may be non-heated. In embodiments, the kale juice may be freeze-thawed, wherein the juiced kale is frozen (typically at around −20° C.—but can be varied) for a period of time and then allowed to thaw (typically by sitting at room temperature to prevent exposure to extreme heat). The freeze-thawed cycle may be performed any number of times prior to incorporation into the chemopreventative composition, and in particular embodiments, may be performed 6 or 7 times. It is envisioned that the kale juice of the chemopreventative compositions may be processed using any of the manners described herein alone or in any combination.

In particular embodiments, the chemopreventative composition includes kale juice having a concentration ranging from about 0.1 µL/mL to about 1000 µL/mL. In embodiments, the concentration of the kale in the chemopreventative composition can range from about 0.75 µL/mL to about 750 µL/mL. In still other embodiments, the concentration of the kale in the chemopreventative composition can range from about 1 µL/mL to about 500 µL/mL. In particular embodiments, the concentration of the juiced kale may be from about 5 µL/mL to about 400 µL/mL. In still other embodiments, the concentration of the kale in the chemopreventative composition can range from about 7 µL/mL to about 200 µL/mL.

In addition to the kale, and in particular embodiments kale juice, the chemopreventative compositions described herein may further include at least one of a pharmaceutically acceptable carrier, a surfactant, an optional ingredient, and/or an additional therapeutic agent.

As used herein the term "pharmaceutically acceptable carrier" refers to a non-toxic solid, semisolid or liquid filler, diluent, encapsulating material, formulation auxiliary, or excipient of any conventional type. A pharmaceutically acceptable carrier is nontoxic to recipients at the dosages and concentrations employed and is compatible with other ingredients of the composition. Some well known pharmaceutically acceptable carriers include, but are not limited to, saline, phosphate buffered saline, water, dextrose, and lactated ringers. Additionally, such pharmaceutically acceptable carriers may be aqueous or non-aqueous solutions, suspensions, colloids, and emulsions. Examples of non-aqueous solvents are alcohols, propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Topical carriers include creams, ointments, gels, jellies, solutions, and the like.

Preservatives and other additives may also be present, such as, for example, antimicrobials, antioxidants, collating agents, inert gases and the like.

In embodiments, the chemopreventative composition may be in the form of a solution or suspension. It is envisioned that the chemopreventative composition, solution or suspension may be applied topically or orally ingested.

In embodiments, a topical skin treatment may be created by combining the juiced kale with the appropriate surfactants to maintain contact between the skin surface and kale juice. Commonly used surfactants appropriate for personal care products include, but are not limited to sodium lauryl sulfate, ammonium laureth sulfate, disodium lauryl sulfosuccinate, cocamphocarboxyglycinate, cocoamidopropyl betaine, and alpha-olefin sulfonate. Alternatively, surfactants made from plant-derived oils may be used instead of surfactants made from petroleum or synthetic oils. These plant derived oils may also be combined with ethoxylates to increase performance. Coloring agents and fragrances may be added to produce a more marketable product.

A chemopreventative spot treatment including juiced kale may also be created. By combining kale with the appropriate surfactants discussed above a more concentrated kale juice product could be created for spot treating small areas a customer fears may contain melanoma cells. This product may have fewer coloring and fragrance concerns but may still need to include the necessary surfactants to allow for long term contact between the kale juice composition and any potentially cancerous or precancerous cells.

Further application of the disclosed research could include a spa treatment involving the combination of the chemopreventative composition including kale juice and appropriate surfactants, which may include muds or clays to treat large portions of a person's body topically. A person may submerge himself in a large container, possibly a bathtub, containing a combination of kale juice and the appropriate surfactants, adjuvants, colorants, or fragrances.

The surfactant may represent from 0% by weight to about 25% by weight of the chemopreventative composition. In embodiments, the surfactant may represent from about 0.01% by weight to about 20% by weight of the chemopreventative composition. In still other embodiments, the surfactant may represent from about 1% by weight to about 10% by weight of the chemopreventative composition.

In embodiments, the chemopreventative compositions may include at least one optional ingredient. Some examples of useful optional ingredients include, but are not meant to be limited to, pH-modifiers, emulsifiers, lyposomes, microspheres, beads, viscosity enhancers, humectants, colors, fragrances, and the like. The optional ingredients typically represent less than about 10% by weight of the composition, in embodiments, less than about 5% by weight of the composition.

It is further envisioned that the chemopreventative compositions described herein may also be administered by intravenous, intraarterial, intramuscular or intratumoral injection of a liquid preparation, oral administration of a liquid or solid preparation including oral solutions, tablets, or capsules for oral ingestion, or by spray solution suitable for nasal spray, oral spray, topical spray, or rectal spray. Administration can also be accomplished by use of a rectal suppository or a urethral suppository.

A range of carrier mediums would be suitable for the topical administration of the chemopreventative compositions described herein. This would include ointments, creams, gels, jellies or other application. The properties of a suitable topical formulation would be one that is easy to apply to a reasonable large area of tissue, requiring the minimum of rubbing and lasting in contact with the tissue from at least a few hours to a few days.

It is further envisioned that the chemopreventative compositions described herein may further include at least one therapeutic agent in addition to the juiced kale. Some non-limiting examples of suitable therapeutic agents include: analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthmatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, phenelzine, desipramine, nortriptyline, tranylcypromine, fluoxetine, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconazole, amphotericin B, nystatin, and candicidin); antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, deflazacort, celecoxib, rofecoxib, hydrocortisone, prednisolone, and prednisone); antineoplastics (e.g., cyclophosphamide, actinomycin, bleomycin, dactinomycin, daunorubicin, doxorubicin, epirubicin, mitomycin, methotrexate, fluorouracil, gemcitabine, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, goserelin, leuprolide, tamoxifen, interferon alfa, retinoic acid (ATRA), nitrogen mustard alkylating agents, and piposulfan); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, propanolol, isometheptene mucate, and dichloralphenazone); sedatives/hypnotics (e.g., barbiturates such as pentobarbital, pentobarbital, and secobarbital; and benzodiazapines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentearythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine); antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenytoin, phenytoin sodium, clonazepam, primidone, phenobarbital, carbamazepine, amobarbital sodium, methsuximide, metharbital, mephobarbital, mephenytoin, phensuximide, paramethadione, ethotoin, phenacemide, secobarbital sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and); agents useful for calcium regulation (e.g., calcitonin, and parathyroid hormone); antibacterial agents (e.g., amikacin sulfate, aztreonam, chloramphenicol, chloramphenicol palmitate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime axetil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; macrolides such as, azithromycin, clarithromycin, and erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and theophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; salmeterol; xinafoate; triamcinolone; nedocromil sodium; flunisolide; fluticasone propionate; steroidal compounds and hormones (e.g., androgens such as danazol, testosterone cypionate, fluoxymesterone, ethyltestosterone, testosterone enathate, methyltestosterone; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and thyroid hormones such as levothyroxine sodium); hypoglycemic agents (e.g., human insulin, purified beef insulin, purified pork insulin, glyburide, metformin, chlorpropamide, glipizide, tolbutamide, and tolazamide); hypolipidemic agents (e.g., clofibrate, dextrothyroxine sodium, probucol, pravastitin, atorvastatin, lovastatin, sodium, and niacin); proteins (e.g., DNase, alginase, superoxide dismutase, and lipase); nucleic acids (e.g., sense or anti-sense nucleic acids encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); as well as other drugs useful in the compositions and methods described herein include mitotane, halonitrosoureas, anthrocyclines, ellipticine, ceftriaxone, ketoconazole, ceftazidime, oxaprozin, valacyclovir, urofollitropin, famciclovir, flutamide, enalapril, itraconazole, buspirone, gabapentin, fosinopril, tramadol, acarbose, lorazepam, follitropin, omeprazole, fluoxetine, lisinopril, tramadol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainide, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide; and combinations thereof.

The therapeutic agents may be used in amounts that are therapeutically effective, which varies widely depending largely on the particular therapeutic agent being used. The amount of therapeutic agent incorporated into the composition also depends upon the desired release profile, the concentration of the agent required for a biological effect, and the length of time that the therapeutic agent should be released for treatment.

The kale and the pharmaceutically acceptable carrier, the surfactant, the optional ingredient and/or the therapeutic agent may be combined in any manner known to those of ordinary skill in the art and suitable for forming the chemopreventative composition. Some non-limiting examples include simply mixing the ingredients prior to, during or after juicing. In other examples the ingredients may be mixed with the kale individually and sequentially. In embodiments, the ingredients of the chemopreventative composition may simply blend together in a manner wherein the ingredients do not chemically interact to form bonds. Alternatively, at least some of the ingredients may chemically interact to forms bonds in the chemopreventative compositions.

The chemopreventative compositions described herein may be formulated to be compatible with the intended route of administration. For example, topical applications may be formed into sterile or non-sterile solutions depending upon the tissue being applied. For example, topical application to the external tissue of a patient's skin does not necessarily have to be sterilized. However, topical application of an inhalation powder or spray and/or application in the form of an eye drop may require sterilization. In embodiments, wherein the chemopreventative composition is sterilized, the composition may be exposed to UV radiation and/or microfiltering process.

In additional examples, the compositions may be formed into orally-ingesting forms, including oral solutions, tablets, capsules, dissolvable films, etc., and thus may not require sterilization.

In still other embodiments, the composition may be intended to be injected, i.e., intramuscularly, intravenously, subcutaneously, intratumorally, intralesionally, the composition may be formed into sterile solutions, suspensions, dispersions, or emulsions including carriers or diluents such as water for injection, saline solution, polyethylene glycols, glycerine, propylene glycol or other synthetic solvents; anti-bacterial agents such as benzyl alcohol or methylparabens; antioxidants such as ascorbic acid or sodium bisulfate; buffers such as acetates, citrates or phosphates, and agents for the adjustment of tonicity such as sodium chloride or dextrose. The pH may be adjusted with acids or bases, such as hydrochloric acid or sodium hydroxide, as needed. Preparations may be enclosed in ampules, disposable syringes or multiple dose vials made of glass or plastic.

The chemopreventative compositions described herein may be stored in a kit, container, pack or dispenser. In some embodiments, the kit may include multiple containers wherein the juiced kale and any additional ingredients may be stored separately and combined immediately prior to use to prolong shelf-life of the ingredients of the composition. In some embodiments, the ingredients of the chemopreventative compositions may be combined prior to storage and contained in a single container. In yet other embodiments, the ingredients of the chemopreventative compositions may be combined prior to storage and stored in multiple containers representing individual doses of the chemopreventative composition.

In addition to the chemopreventative compositions described herein, the kits may also include additional tools or objects including, but not limited to, a syringe, a needle, a straw, delivery tools such as a pad or sponge for topical delivery, measuring cups or mixing cups for orally-ingested solutions. The compositions included in kits may be supplied in containers of any sort such that the life of the different components may be preserved and may not be adsorbed or altered by the materials of the container. For example, sealed glass ampules or vials may contain the compositions described herein that have been packaged under a neutral non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include bottles that are fabricated from similar substances as ampules, and envelopes that consist of foil-lined interiors, such as aluminum or an alloy. Other containers include test tubes, vials, flasks, bottles, syringes, etc. Some containers may have a sterile resealable access port, such as a bottle having a stopper that may be pierced repeatedly by a hypodermic injection needle.

The present disclosure further provides methods of use of a chemopreventative compositions described herein, such as for 1) treating a mammalian subject with cancer; 2) suppressing or inhibiting cancer in a mammalian subject; 3) reducing the risk of developing cancer in a mammalian subject; 4) treating precancerous lesions in a mammalian subject; 5) suppressing or inhibiting precancerous lesions in a mammalian subject; 6) reducing the amount of precancerous lesions in a mammalian subject; by administering the chemopreventative compositions as provided hereinabove; 7) reducing the amount of cancer and/or precancerous lesions in a mammalian subject, by topically applying the chemopreventative composition to the cancer and/or precancerous lesion; 8) being non-toxic to non-cancerous cells; and, 9) increasing the amount of non-cancerous cells. In one embodiment the subject is a mammalian subject. In another embodiment the subject is a human subject.

The present disclosure also provides methods of use of a chemopreventative compositions described herein, such as for 1) treating a mammalian subject with melanoma; 2) suppressing or inhibiting melanoma in a mammalian subject; 3) reducing the risk of developing melanoma in a mammalian subject; 4) treating premelanoma lesions in a mammalian subject; 5) suppressing or inhibiting premelanoma lesions in a mammalian subject; 6) reducing the amount of premelanoma lesions in a mammalian subject; by administering the chemopreventative compositions as provided hereinabove; 7) reducing the amount of melanoma and/or premelanoma lesions in a mammalian subject, by topically applying the chemopreventative composition to the melanoma and/or premelanoma lesion; 8) reducing the amount of melanoma and/or premelanoma lesions in a mammalian subject, by orally-ingesting the chemopreventative composition on a daily basis for at least week, month, and/or year; 9) being non-toxic to non-cancerous epithelial; and, 10) increasing the amount of non-cancerous epithelial cells. In one embodiment the subject is a mammalian subject. In another embodiment the subject is a human subject.

The present disclosure also provides methods of use of a chemopreventative compositions described herein, such as for 1) treating a mammalian subject with basal cell carcinoma or skin tags; 2) suppressing or inhibiting basal cell carcinoma or skin tags production in a mammalian subject; 3) reducing the risk of developing basal cell carcinoma or skin tags in a mammalian subject; 4) treating prebasal cell carcinoma or pre-skin tags lesions in a mammalian subject; 5) suppressing or inhibiting prebasal cell carcinoma or pre-skin tags lesions in a mammalian subject; 6) reducing the amount of prebasal cell carcinoma or pre-skin tags lesions in a mammalian subject; by administering the chemopreventative compositions as provided hereinabove; 7) reducing the amount of basal cell carcinomas, prebasal cell carcinoma, skin tags, or pre-skin tag lesions in a mammalian subject, by topically applying the chemopreventative composition to the basal cell carcinomas, prebasal cell carcinoma, skin tags, or pre-skin tag lesion; 8) reducing the amount of basal cell carcinomas, prebasal cell carcinoma, skin tags, or pre-skin tag lesions in a mammalian subject, by orally-ingesting the chemopreventative composition on a daily basis for at least week, month, and/or year; 9) being non-toxic to non-cancerous epithelial cells; and, 10) increasing the amount of non-cancerous epithelial cells. In one embodiment the subject is a mammalian subject. In another embodiment the subject is a human subject.

In one embodiment, a method of inducing apoptosis in cancer cells includes applying a chemopreventative composition including kale juice to cancer cells. The kale of the chemopreventative composition may be selected from the group consisting of curly kale, baby kale, organic kale, kale harvested during seeding time, and combinations thereof.

In embodiments, the kale of the chemopreventative composition includes curly kale.

In embodiments, the kale juice of the chemopreventative composition is unfiltered.

In embodiments, the kale juice of the chemopreventative composition includes freeze-thawed kale.

In embodiments, the kale juice of the chemopreventative composition includes sonicated kale.

In embodiments, the kale juice of the chemopreventative composition includes non-heated kale.

In embodiments, the cancer cells are selected from the group consisting of melanoma cells, breast cancer cells, colon cancer cells, ovarian cancer cells, prostate cancer cells, brain cancer cells, bone cancer cells, bladder cancer cells, testicular cancer cells, thyroid cancer cells, lung cancer cells, liver cancer cells, pancreatic cancer cells, throat cancer cells, and combination thereof.

In embodiments, the cancer cells include melanoma cells.

In embodiments, the step of applying the chemopreventative composition includes topical delivery of the composition.

In embodiments, the method of inducing apoptosis in cancer cells further includes applying the chemopreventative composition to non-cancerous cells, wherein the chemopreventative composition is non-toxic to the non-cancerous cells and/or the chemopreventative composition promotes the growth of the non-cancerous cells.

In embodiments, the non-cancerous cells are epithelial cells.

In embodiments, the method of inducing apoptosis in cancer cells further includes maintaining interaction between the chemopreventative composition and the cancer cells for more than 7 hours.

In embodiments, the method of inducing apoptosis in cancer cells further includes maintaining interaction between the chemopreventative composition and the cancer cells for more than 20 hours.

In embodiments, the method of inducing apoptosis in cancer cells includes that the chemopreventative composition further includes at least one of a pharmaceutically acceptable carrier or a surfactant.

In embodiments, a chemopreventative composition for inducing apoptosis in cancer cells includes kale juice, and at least one of a pharmaceutically acceptable carrier or a surfactant.

In embodiments, the kale juice includes a particle size ranging from about 25 microns to about 500 microns, from about 30 microns to about 300 microns, or about 35 microns to about 200 microns.

In embodiments, the pharmaceutically acceptable carrier is selected from the group consisting of water, saline, Ringer's Lactate solutions and dextrose solution.

In embodiments, the surfactant is selected from the group consisting of sodium lauryl sulfate, ammonium laureth sulfate, disodium lauryl sulfosuccinate, cocamphocarboxyglycinate, cocoamidopropyl betaine, alpha-olefin sulfonate, and combinations thereof.

In embodiments, the composition is a topical solution, wherein the topical solution includes a concentration of the kale juice ranging from about 0.1% by wt to about 95% by wt or from about 1% by wt to about 90% by wt.

In embodiments, the topical solution includes a concentration of the kale juice below 400 uL/mL.

In embodiments, the solution includes a concentration of the kale juice below about 15 uL/mL.

In embodiments, the composition is deliverable to the cancer cells in a form selected from the group consisting of intravenously, intramuscularly, subcutaneously, intratumorally, topically, orally, transdermally, sublingually, via nasal inhalation, via oral inhalation, via suppository, and combinations thereof.

In embodiments, the composition induces apoptosis in cancer cells selected from the group consisting of melanoma cells, breast cancer cells, colon cancer cells, ovarian cancer cells, prostate cancer cells, brain cancer cells, bone cancer cells, bladder cancer cells, testicular cancer cells, thyroid cancer cells, lung cancer cells, liver cancer cells, pancreatic cancer cells, throat cancer cells, and combination thereof.

In embodiments, the composition induces apoptosis in cancer cells including melanoma cells.

In embodiments, the chemopreventative composition is non-toxic to non-cancerous cells.

In embodiments, the chemopreventative composition promotes growth of the non-cancerous cells.

In embodiments, the non-cancerous cells are epithelial cells.

In embodiments, the chemopreventative composition further includes a therapeutic agent.

In embodiments, the chemopreventative composition further includes at least one optional ingredient selected from the group consisting of pH-modifiers, emulsifiers, lyposomes, microspheres, beads, viscosity enhancers, humectants, dyes, fragrances, preservatives, and emollients.

In embodiments, a method of reducing cancerous or precancerous skin lesions includes orally-ingesting a chemopreventative composition including a kale solution.

In embodiments, the orally-ingested kale of the chemopreventative composition is selected from the group consisting of curly kale, baby kale, organic kale, kale harvested during seeding time, and combinations thereof.

In embodiments, the kale of the chemopreventative composition for reducing cancerous or precancerous skin lesions is selected from the group consisting of blended kale, juiced kale, sonicated kale, frozen kale, filtered kale, sterilized kale, and combinations thereof.

In embodiments, the cancerous or precancerous skin lesions include basal cell carcinoma.

In embodiments, the cancerous or precancerous skin lesions include skin tags.

In embodiments, the chemopreventative composition is non-toxic to non-cancerous and non-precancerous cells.

In embodiments, the chemopreventative composition promotes the growth of the non-cancerous and non-precancerous cells.

In embodiments, the non-cancerous cells are epithelial cells.

In embodiments, the method of reducing cancerous or precancerous skin lesions, further includes repeating the step of orally-ingesting the chemopreventative composition on at least a daily basis for at least one week.

In embodiments, the method of reducing cancerous or precancerous skin lesions, further includes repeating the step of orally-ingesting the chemopreventative composition on at least a daily basis for at least one month.

In embodiments, the method of reducing cancerous or precancerous skin lesions, further includes repeating the step of orally-ingesting the chemopreventative composition on at least a daily basis for at least three months.

In embodiments, the method of reducing cancerous or precancerous skin lesions, further includes repeating the step of orally-ingesting the chemopreventative composition on at least a daily basis for at least six months.

In embodiments, the method of reducing cancerous or precancerous skin lesions, further includes repeating the step of orally-ingesting the chemopreventative composition on at least a daily basis for at least one year.

In embodiments, the step of orally-ingesting the chemopreventative composition is performed once a day.

In embodiments, the step of orally-ingesting the chemopreventative composition is performed more than once a day.

In embodiments, the step of orally-ingesting the chemopreventative composition is performed twice a day.

In embodiments, the step of orally-ingesting the chemopreventative composition is performed four times a day.

In embodiments, the chemopreventative composition further including at least one of a pharmaceutically acceptable carrier or a surfactant It will be understood that various modifications may be made to the embodiments disclosed herein. For example, the compositions may include more than one type of juiced kale. Thus, those skilled in the art will envision other modifications within the scope and spirit of the claims.

EXAMPLES

Vegetable Acquisition

Vegetable samples were acquired as follows:
  Kale samples were picked from the same organic farm in the winter time.
  Organic green leaf lettuce was acquired at a national chain grocery store.

Vegetable Cleaning

Two methods were used to clean the vegetables, i.e., kale and lettuce, prior to processing.

Soap Method:
A 12 quart dish tub was autoclaved, UV sterilized, and then washed with Dawn® Ultra dishwashing soap and rinsed with water to remove any residues prior to placement of kale leaves. The tub was filled to capacity with 12 quarts of lukewarm water and 1 teaspoon of Dawn® Ultra antibacterial dishwashing soap was added. Approximately 10 kale leaves were washed per 3 gallons of the soapy water mixture. The kale leaves were then agitated by hand in the soapy mixture for approximately 5 minutes. The soapy water was then drained with the kale leaves still in the tub. Then the kale leaves were washed in over 4 gallons of fresh water for a 10 minute period. This kale leaf rinsing procedure was repeated 7 consecutive times. The lettuce was washed the same way as the kale.

Rinsing Method:
The kale leaves were rinsed in cold running water for 15 minutes.

As shown in FIG. 1, for example, the kale leaf (on the right side of the photo) that was cleaned using the soap method has a shinier, glazed appearance than the kale leaf (on the left side of the photo) that was cleaned using the rinse method.

FIG. 1 is a comparison of washing methods of commercial kale. Both kale leaves were washed with equal amounts of water. The leaf on the left was washed in plain tap water and the leaf on the right was washed with Dawn® dishwashing soap.

The kale was processed into many forms including: a blended kale prepared with a blender and a centrifuge; a juiced kale prepared with an electric juicer (which is unfiltered and non-sterile); a sterile, microfiltered juiced kale filtered through a 0.22 micron filter; a sonicated juiced kale prepared with a Q sonicator; a heated juiced kale; a freeze-thaw juiced kale; organic juiced kale; and organic baby juiced kale.

Example 1

Approximately 10 whole kale leaves were packed into a TRU 500 watt blender. 500 mL of deionized water was added. The blender was pulsed for 30 seconds and then rested for 10 seconds to prevent heating of the samples. This process was repeated for 15 minutes. The motor of the blender was turned off and allowed to cool to prevent overheating at the 10 minute mark for 1 minute. A sterile glass rod was utilized to pack down the kale to ensure proper blending. Contents were then decanted into a sterile 1000 mL beaker. The beaker was kept on ice to keep the sample cool. The blended kale extract was then poured using a sterile funnel into 16 sterile 50 mL centrifuge tubes. The centrifuge tubes were centrifuged at 2500 rpm at 4° C. for 5 minutes. The supernatant was decanted into another sterile 1000 mL beaker. The fluid was then divided into 50 mL centrifuge tubes and centrifuged at 3500 rpm at 4° C. for 10 minutes. The resulting supernatant was decanted into another sterile 1000 mL beaker (volume=400 mL) and then divided into aliquots of various sizes and stored at −20° C.

Example 2

Cleaned whole kale leaves were juiced using a Breville® IKON BJE510XL electric juicer that contained a stainless steel micromesh filter. The juicer was used due to its consistent quality, speed, and efficacy in producing kale juice. Curly kale is known to be a fibrous vegetable and placed a considerable strain on most juicer motors. Pulp came out relatively dry resembling sawdust. All of the juicer components were sterilized with a UV lamp and then washed with Dawn® Ultra antibacterial dishwashing soap to remove any residues. The kale leaves were slowly juiced at the setting of 1. Higher speeds resulted in occasional chunks landing in juiced sample. Multiple plastic bags were placed in the bin to ease removal of pulp as the container filled up. After the juice was collected into sterile containers 50 mL conical centrifuge tubes, it was stored at −20° C. Several days later, it was thawed and divided into smaller aliquots of 150 µL and then frozen again. The juicer was promptly sterilized and cleaned after use. The brush and spatula tool provided with the juicer were used to remove remaining pulp. The micromesh filter tends to hold water after washing. To dry it, the machine was reassembled without the pulpcatching bin and food pusher. It was run for a minimum of 5 minutes at the high speed setting of 5. Juicer sterilization: disassembled clean juicer into a 4 gallon dishwashing tray. Placed under UV light and sterilized for 30 minutes, then carefully removed.

Example 3

The kale juice produced from Example 2 was filter sterilized through a 0.22 micron filter into a sterile conical tube to produce a sterile, microfiltered juiced kale.

Example 4

The kale juice produced from Example 2 was sonicated on ice 7 times for 10 seconds with a Q sonicator (125 Watts) set at 70% of 20 kHz (Fisher Scientific). The sonicated kale juice was then filter sterilized through a 0.22 micron filter to produce a sterile sonicated juiced kale.

Example 5

The kale juice produced from Example 2 was heated for 15 minutes in a deionized water bath heated to a temperature of 100° C. to produce a heated juiced kale.

Example 6

The kale juice produced from Example 2 was frozen and then allowed to thaw at room temperature thereby constituting one freeze-thaw cycle to produce freeze-thawed juiced kale.

Example 7

Organic kale was juiced as described in Example 2 to produce organic juiced kale.

Example 8

Organic baby kale was juiced as described in Example 2 to produce organic baby juiced kale.

Example 9

Quantification of Chlorophyll Content and Normalization of Kale Juice to Lettuce Juice The contents of kale juice and lettuce juice differ dramatically. The chlorophyll A content was used as a standard for the mass of material in each juice preparation. Chlorophyll was extracted with acetone and measured with a UV-VIS spectrophotometer (Hewlett Packard/Agilent 8453 Diode Array UV-Visible Spectrophotometer). To extract the chlorophyll content of the samples, 10 mL of 80% acetone was added to 0.5 g of kale juice or lettuce juice. The solutions were centrifuged for 5 minutes at 2500 rpm at 4° C. and the supernatants were transferred to new vials. The absorbance at 660 nm at of one mL of the each sample was obtained. The Axwavelength of 80% acetone was measured as a "blank". The green leaf lettuce juice was normalized to the kale juice by dilution with 80% acetone until the chlorophyll peaks matched at 1 unit.

Example 10

B16F10 mouse melanoma cells were grown in an incubator at 37° C. with 5% Carbon dioxide ($CO_2$) in RPMI with 5% fetal bovine serum (FBS), 1.5 g/L sodium bicarbonate, 2 mM L-glutamine, and 1% penicillin/streptomycin—hereafter referred to as control medium. The cell line was purchased from the American Type Culture Collection.

Dose Response:

On day one, 100,000 B16F10 cells (from Example 9) per well (4 replicates per treatment) were seeded in 24 well plates with 1 mL of control medium (RPMI with 5% FBS) and incubated for 24 hours. On day two, medium was exchanged for RPMI 0.5% FBS with an overnight incubation. On day three, the control and experimental media were added. Five different concentrations were tested: 10%, 20%, 30%, 40%, and 100%, with RPMI 5% FBS as the diluent. The different types of kale juices were added to the cells, which were incubated for another 24 hours. On day four, cells were collected by trypsinizing and resuspending the cells in 50 μL medium for counting. A Nexcelom AutoT4 automated cell counter was used per the manufacturer's instructions.

Cell Growth Measurements:

75 $cm^2$ cell culture flasks were used to grow the B16F10 mouse melanoma cells because this would allow enough space for the flask to reach confluency over the course of a week. Each flask was seeded with 200,000 cells in 13 mL of control medium. On day two, medium was exchanged for RPMI 0.5% FBS to synchronize the cells with an overnight incubation. The different types of kale juices were added and cells were incubated for 24 hours. Each day, the medium was replenished by aspirating the day old medium, washing the cells with PBS, and then adding fresh medium with juice. Flasks were inspected each day with a tissue culture microscope (Motic) to monitor morphological changes or cell death. Cells were collected for counting at four days as described above with these changes: 7 mL of PBS for washing, 3 mL of trypsin, and 5 mL of medium. The number of cells, mean cell diameter, and cell concentration/mL were recorded. The experiment was repeated three times.

Green leaf lettuce juice was used as a control vegetable juice. Cells were treated with each juice for three days and then collected and counted. The kale juice treatments for these experiments consisted of juiced kale, sonicated juiced kale, juice from locally grown organic kale (free from any herbicides, insecticides, or fertilizer), organic baby kale that was purchased from a national chain grocery store.

A second set of cell count experiments was generated using 24-well plates. Briefly, each well was plated with 200,000 cells in 500 μL of RPMI 5% FBS. Each well was allowed a 24 hour "attachment" period. Cells were synchronized with RPMI 0.5% FBS overnight. After 24 hours, the medium was exchanged for control or experimental media. A 0.7% solution of each kale juice was added. The medium was changed daily by washing the cells with PBS before the application of fresh kale juice. Flasks were inspected each day with a tissue culture microscope to monitor any changes and collected for counting as previously described. Each experiment was repeated at least three times.

Figure 2A:
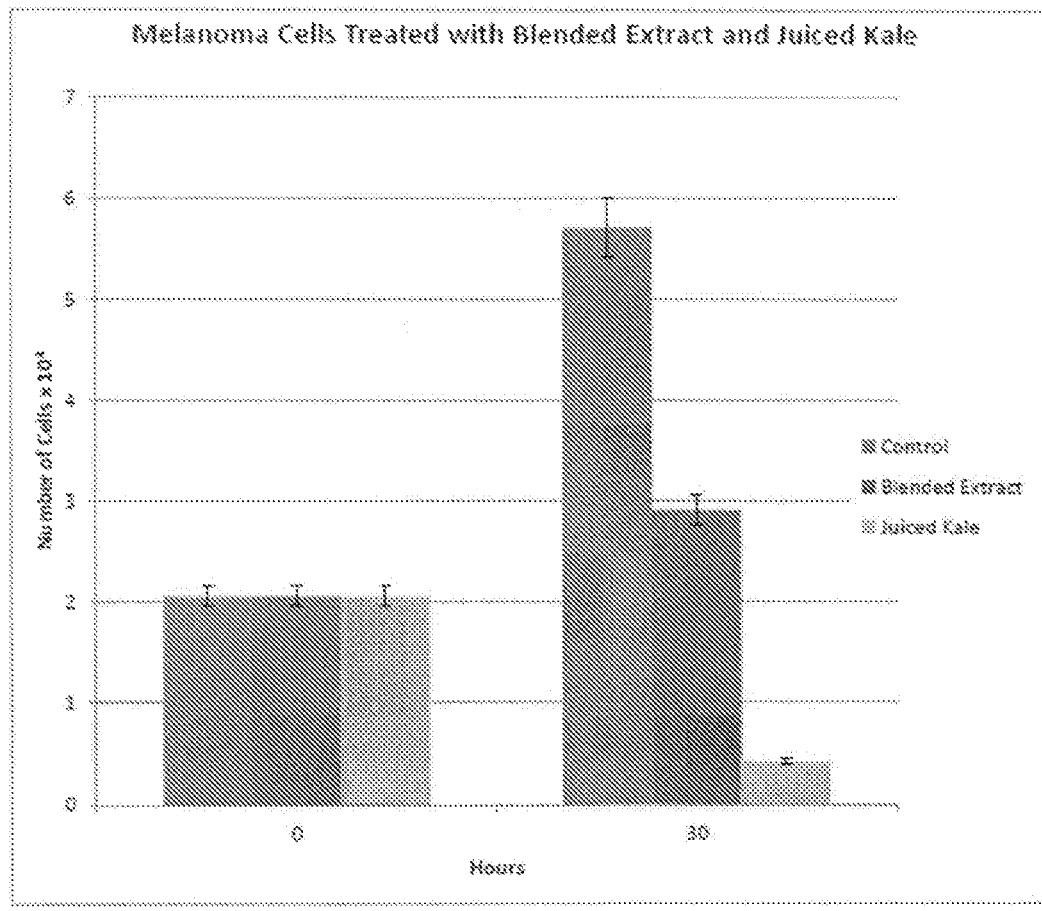
FIG. 2A is a bar graph reflecting a comparison of the ability of unfiltered juiced kale, blended kale, and a control to kill melanoma cells.
Figure 2B:
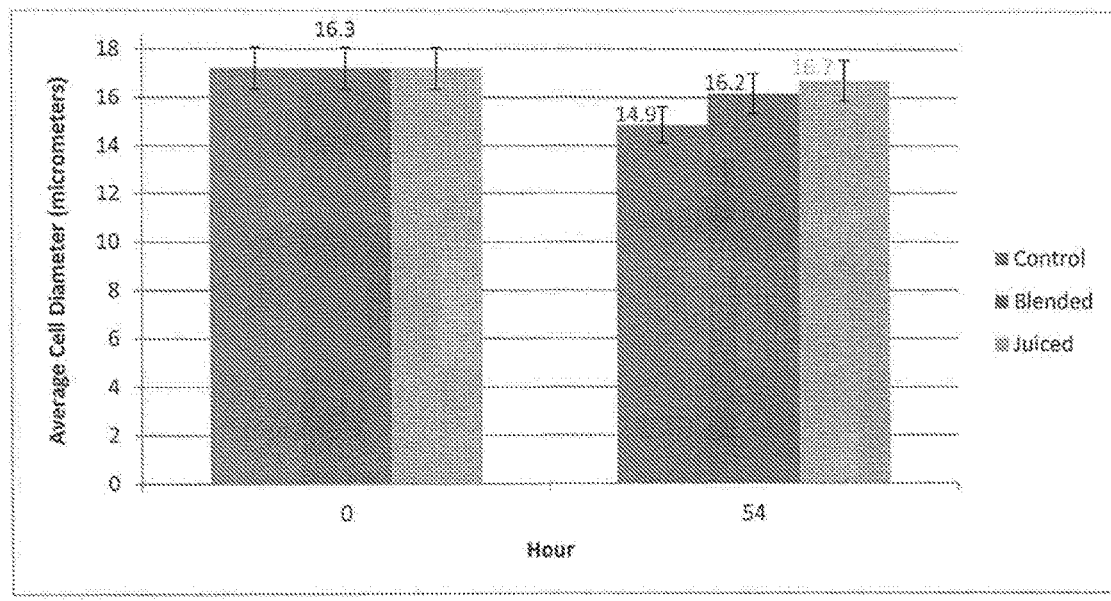
FIG. 2B is a bar graph reflecting a comparison of the average cell diameter of melanoma cells following exposure to unfiltered juiced kale, blended kale, and a control.

FIG. 2A depicts a comparison between unfiltered juiced kale, blended kale, and a control which reveals that juiced kale kills melanoma cells (in vitro) and this response is quite reproducible (the error bar is tight). (ANOVA df=2, F=30.18, p=0.001. Blended Extract p=0.03 Juiced Kale p=0.01 Error bars represent the standard error of the mean.) FIG. 2B depicts a comparison of the average cell diameter after 54 hours between juiced kale, blended kale, and a control which reveals any osmotic effects of the juiced kale treatments. Synchronized B16F10 cells were treated with blended and juiced kale. Cell diameter was measured to monitor any osmotic effects of the kale treatments. Graphs represent the mean of at least 3 independent experiments. Error bars represent the standard error of the mean.

Figure 3A:
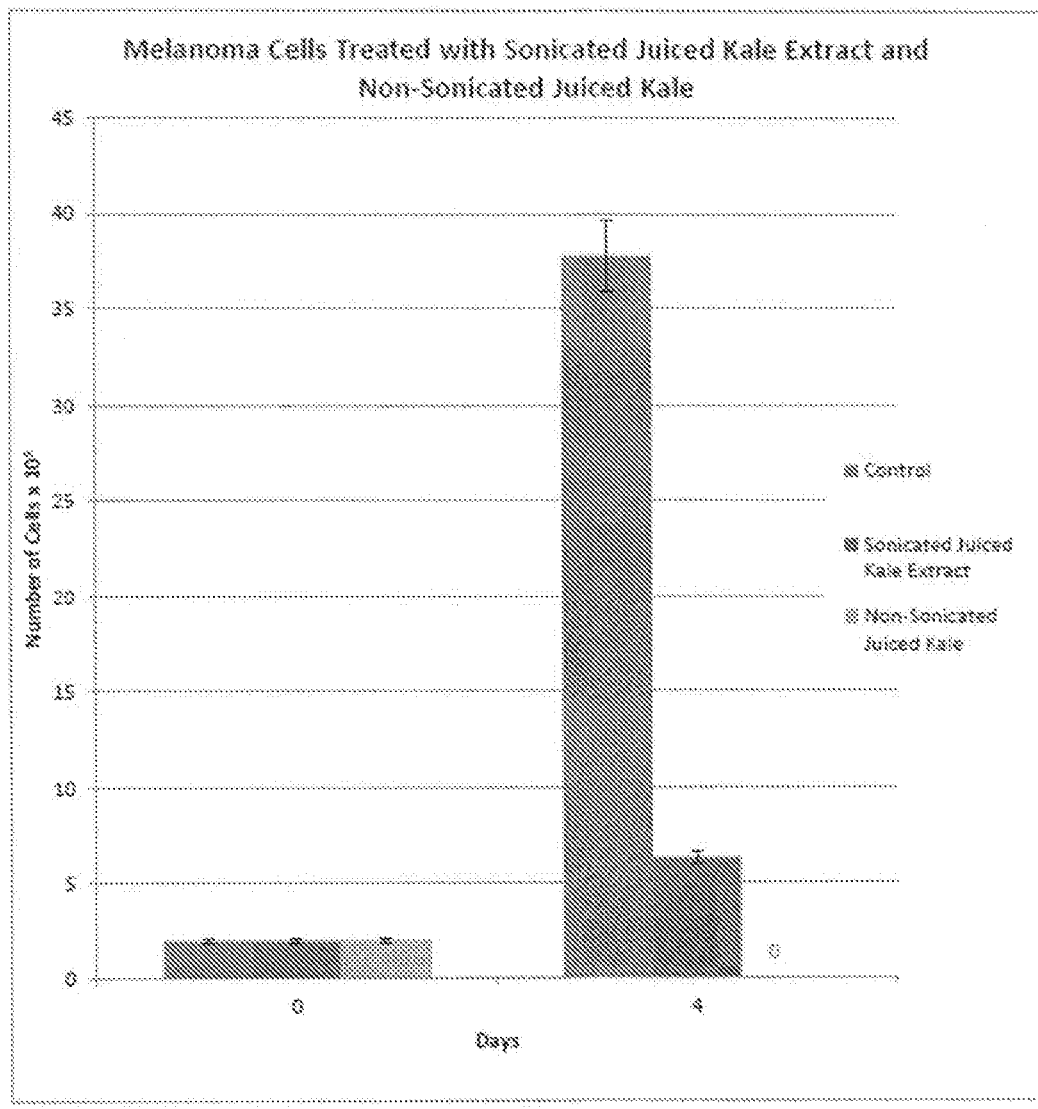
FIG. 3A is a bar graph reflecting a comparison of the ability of unfiltered juiced kale, sonicated kale, and a control to kill melanoma cells.
Figure 3B:
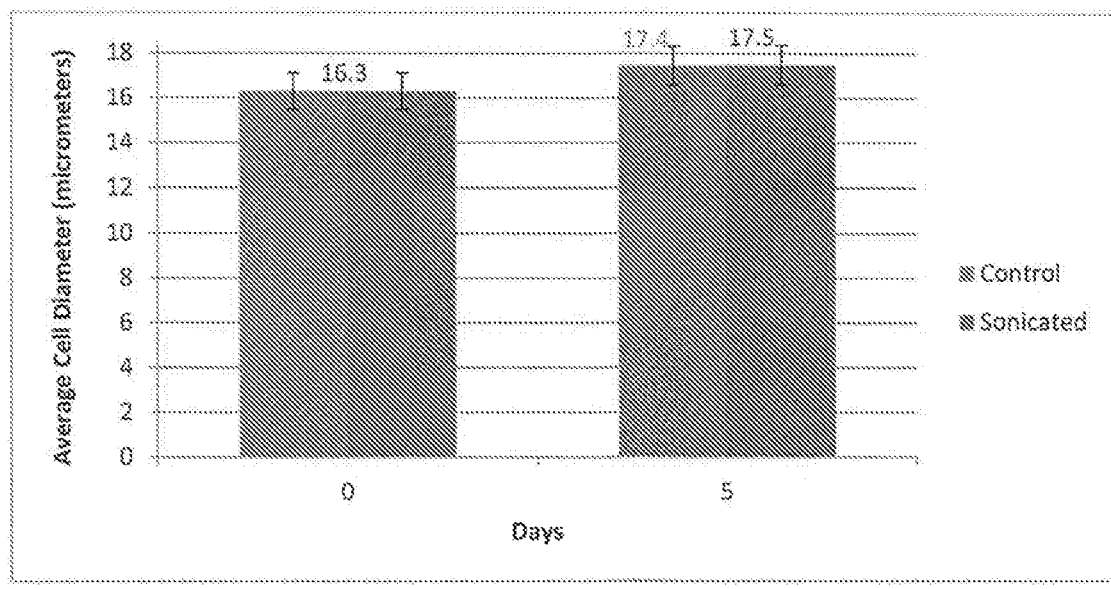
FIG. 3B is a bar graph reflecting a comparison of the average cell diameter of melanoma cells following exposure to sonicated juiced kale and a control.

FIG. 3A depicts a comparison between unfiltered juiced kale (non-sonicated), sonicated kale juice, and a control which reveals that juiced kale kills melanoma cells (in vitro) and this response is quite reproducible (the error bar is tight). Synchronized B16F10 cells were treated with sonicated juiced kale extract and juiced kale at a 0.7% concentration. Both juices were standardized by weight prior to juicing. FIG. 3A shows a graph of mean cell counts on days 0 and 4 of the experiment. The graph represents the mean of three independent experiments. (ANOVA df=2, F=60.2, p=0.0001. Student T tests: Untreated v. Sonicated juiced kale extract p=0.02. Untreated v. Juiced kale p=0.01 Error bars represent the standard error of the mean.) FIG. 3B depicts a comparison of the average cell diameter after 5 days between sonicated juiced kale and a control which reveals any osmotic effects of the juiced kale treatments. Synchronized B16F10 cells were treated with unfiltered and sonicated kale juice. Cell diameter was measured to monitor any osmotic effects of the kale juice. Graphs represent the mean of at least 3 independent experiments. Error bars represent the standard error of the mean.

Figure 4:
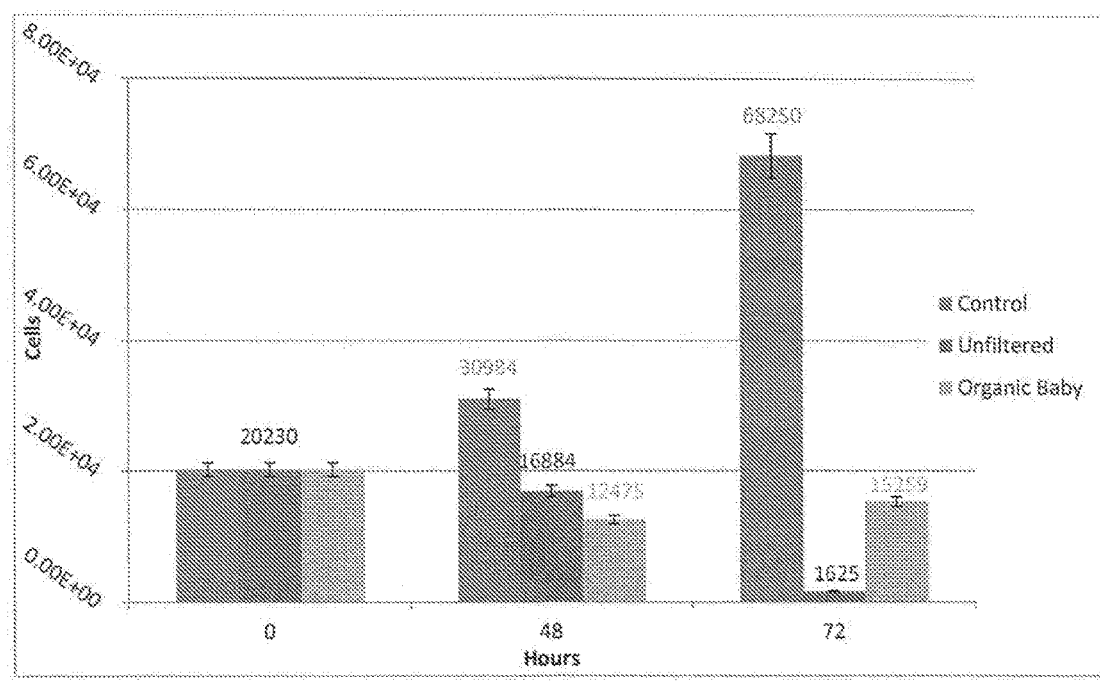
FIG. 4 is a bar graph reflecting a comparison of the ability of unfiltered juiced kale, organic baby kale juice, and a control to kill melanoma cells.

FIG. 4 depicts a comparison between unfiltered juiced kale, organic baby kale, and a control which reveals that juiced kale and organic baby kale juice kill melanoma cells (in vitro) and this response is quite reproducible (the error bar is tight). FIG. 4 is a graph of mean cells numbers on hours 0, 48, and 72 of the experiment. There was no osmotic effect on the cells by the kale treatments (data not shown). Graphs represent the mean of at least 3 independent experiments. Error bars represent the standard error of the mean.

Figure 5:
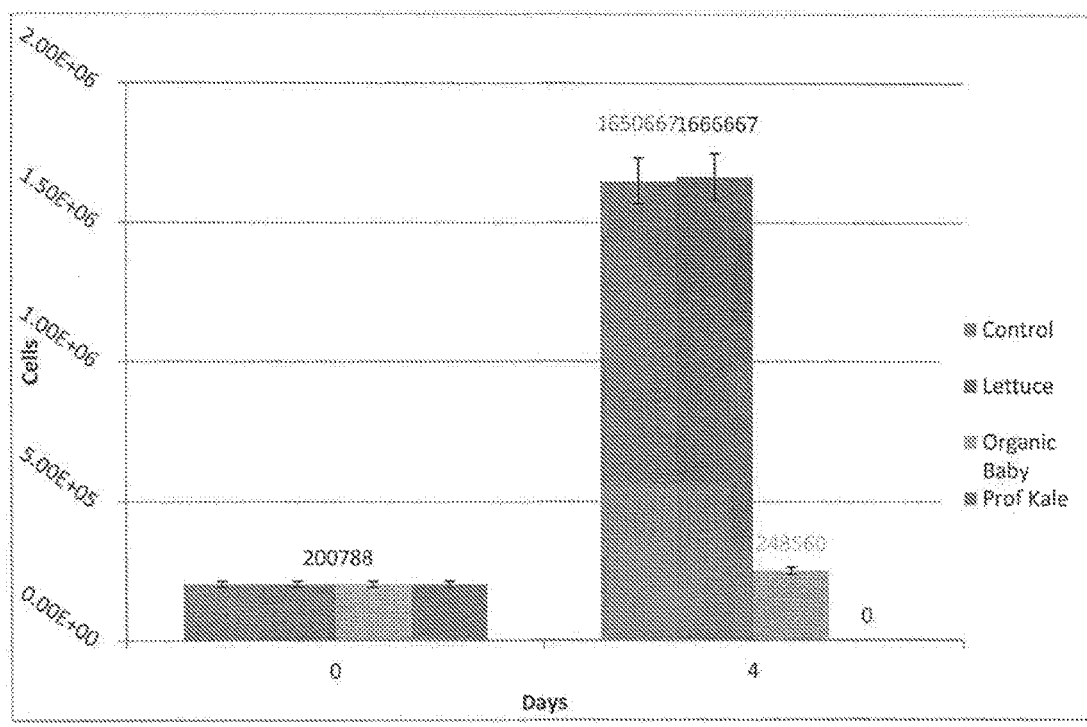
FIG. 5 is a bar graph reflecting a comparison of the ability of unfiltered juiced kale, organic baby kale juice, lettuce juice, and a control to kill melanoma cells.

FIG. 5 depicts a comparison between unfiltered commercially available organic baby kale juice, organic baby kale, lettuce juice and a control which reveals that unfiltered commercially available organic baby kale juice kills melanoma cells (in vitro) and this response is quite reproducible (the error bar is tight). Synchronized B16F10 cells were treated with locally grown organic kale, commercially available organic baby kale, and lettuce juices. Graph of mean cell numbers on days 0 and 4 of the experiment. Cell diameter was measured to monitor any osmotic effects of the juice treatments. There was no osmotic effect on the cells by the juice treatments (data not shown). Graphs represent the mean of at least 3 independent experiments. Error bars represent the standard error of the mean.

Figure 6:
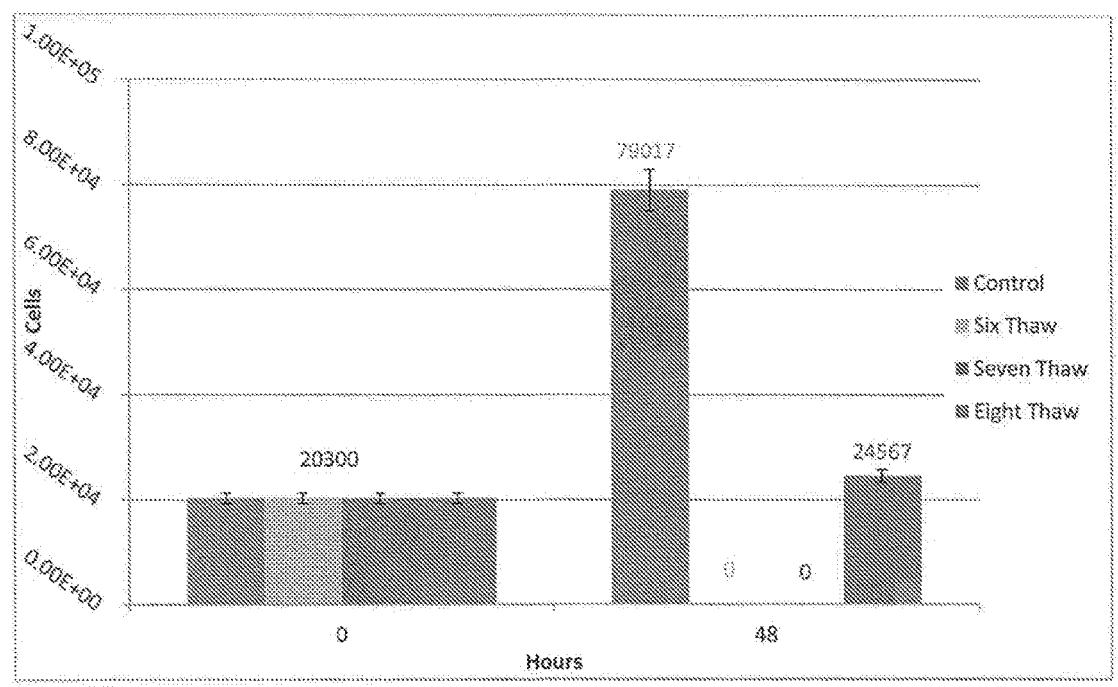
FIG. 6 is a bar graph reflecting a comparison of the ability of a variety of freeze thawed kales and a control to kill melanoma cells.

FIG. 6 depicts a comparison between a variety of freeze-thawed kale juice and a control which reveals that freeze-thawed kale juice (6) and (7) kill melanoma cells (in vitro) and this response is quite reproducible (the error bar is tight). Synchronized B16F10 cells were treated with frozen and thawed kale juices. Graph of mean cell numbers of hours 0 and 48 of the experiment. Cell diameter was measured to monitor any osmotic effects of the juice treatments. There was no osmotic effect on the cells by the juice treatment (data not shown). Graphs represent the mean of at least 3 independent experiments. Error bars represent the standard error of the mean.

Figure 7A:
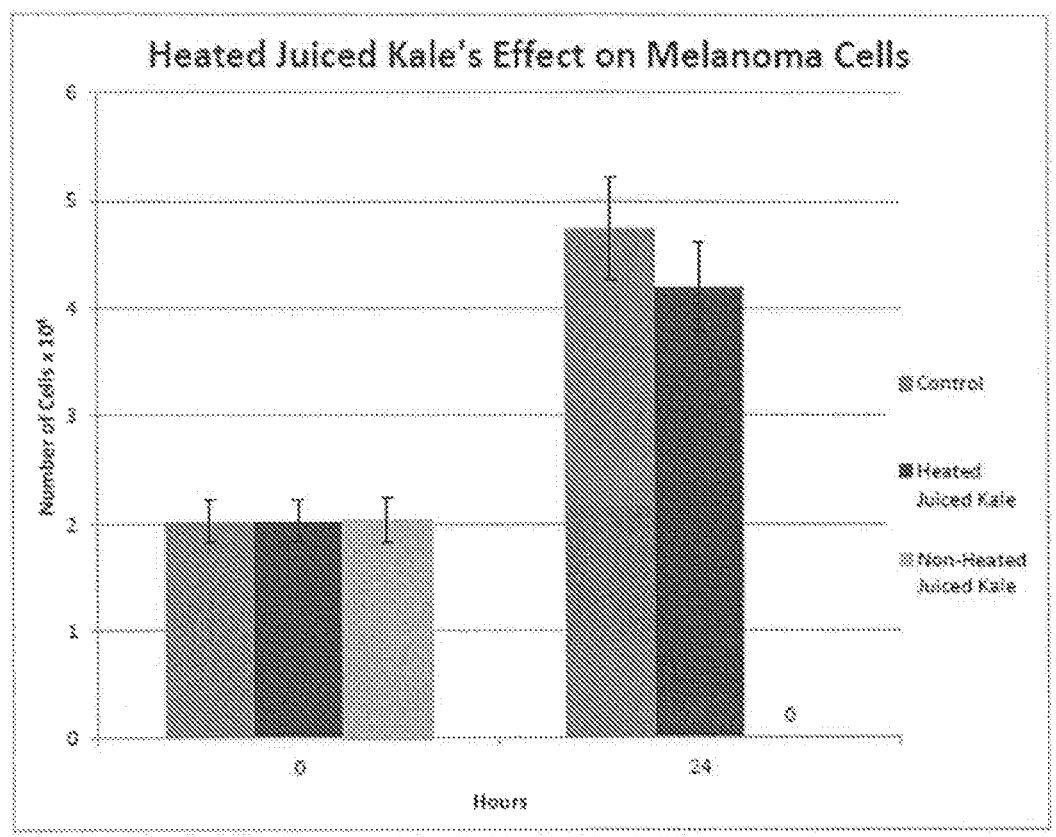
FIG. 7A is a bar graph reflecting a comparison of the ability of non-heated unfiltered juiced kale, heated kale juice, and a control to kill melanoma cells.

FIG. 7A depicts a comparison between unfiltered unheated kale juice, unfiltered heated kale juice, and a control which reveals that unfiltered unheated kale juice kills melanoma cells (in vitro) while unfiltered heated kale juice did not. Synchronized melanoma cells were treated with 0.7% heated juiced kale and juiced kale. Graph of mean cell numbers of hours 0 and 24 of the experiment. Graphs represent the mean of three independent experiments. (ANOVA df=2, F=28.9, p=0.0001. Student T-tests: Untreated v. Heated juiced kale p=0.48. Untreated v. Juiced kale p=0.003 Error bars represent the standard error of the mean.)

Figure 8:
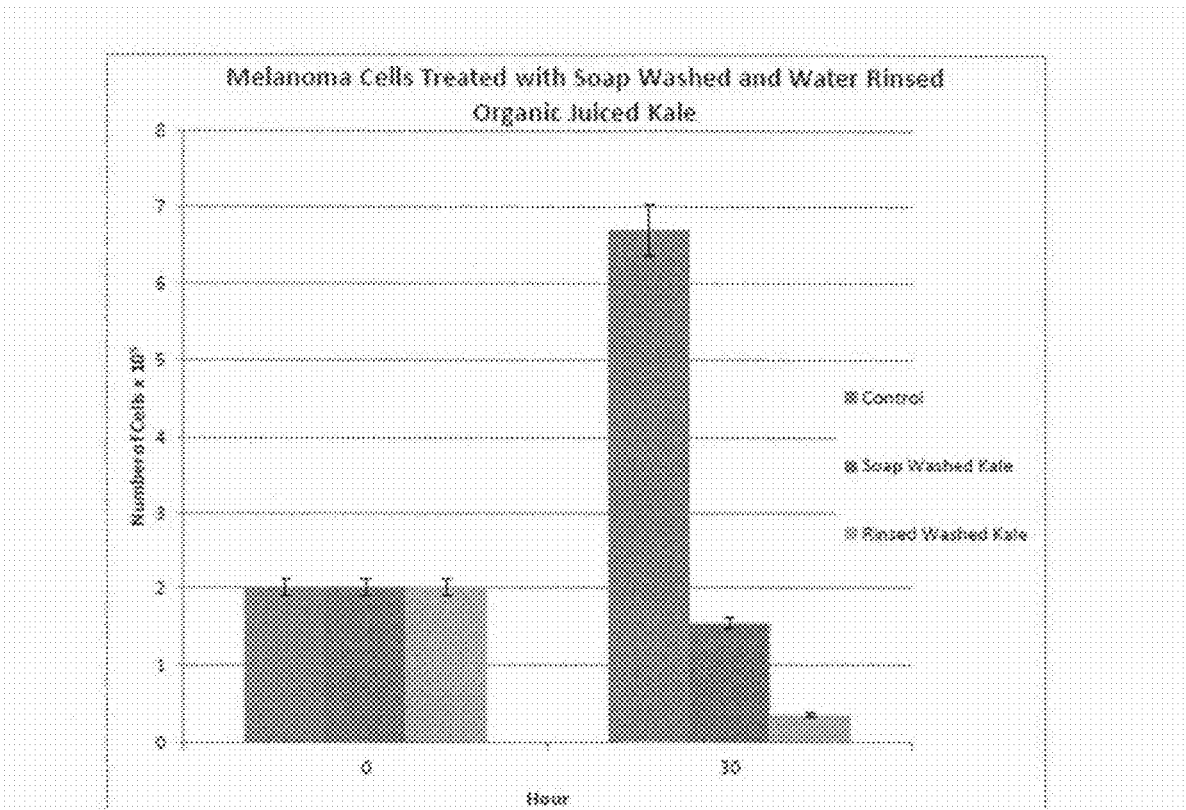
FIG. 8 is a bar graph reflecting a comparison of the ability of rinsed washed unfiltered juiced kale and soap washed unfiltered juiced kale, blended kale, and a control, to kill melanoma cells.
Figures 9A, 9B, 9C, 9D:
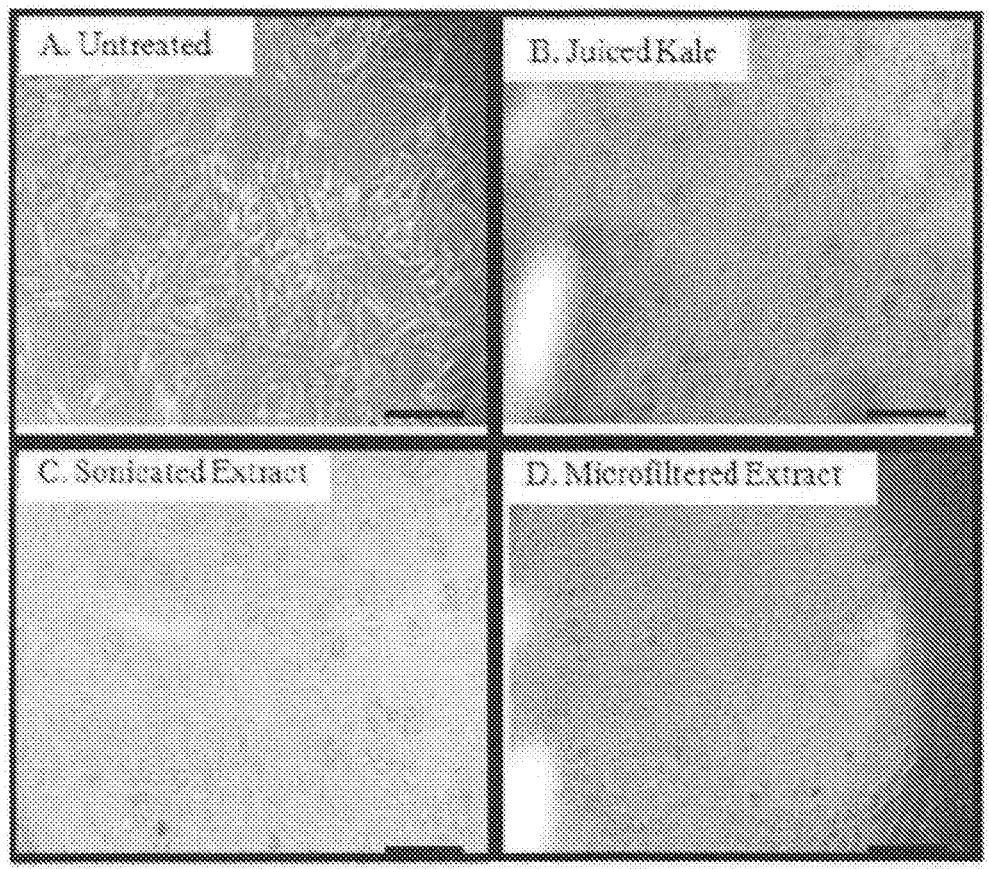
FIGS. 9A-9D are photographic images of untreated melanoma cells and melanoma cells treated with unfiltered juiced kale, sonicated juiced kale, and sterile microfiltered kale juice.

FIG. 8 depicts a comparison between soap washed unfiltered kale juice, rinsed unfiltered kale juice, and a control which reveals that both soap washed and rinsed unfiltered kale juice kills melanoma cells (in vitro).

FIGS. 9A-9D are images at 20× magnification shown untreated and 96 hours after treatment with a 0.7% vol/vol solution of juiced kale (9B), sonicated kale (9C) and microfiltered. Images were obtained at 20× magnification with a Motic inverted microscope equipped with phase contrast, 96 hours after treatment with a 0.7% vol/vol solution. Scale bar is equal to 100 micrometers.

Figure 10A:
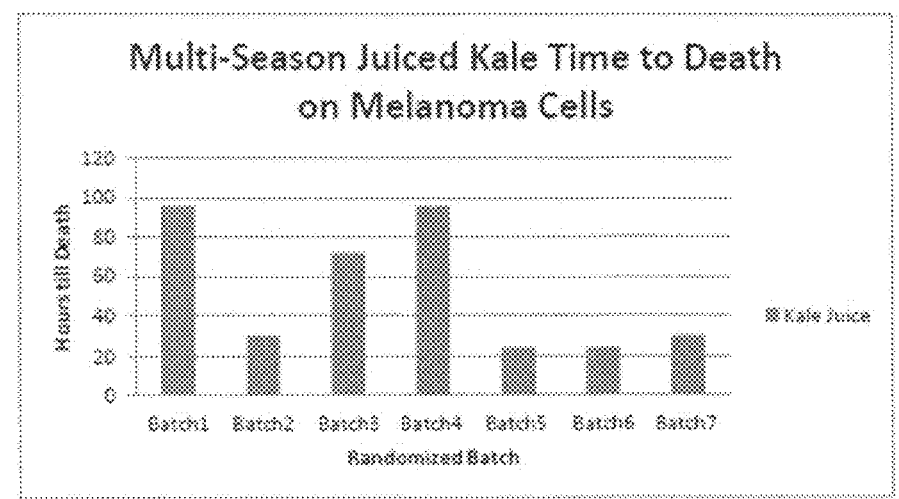
FIG. 10A is a bar graph reflecting a comparison of the randomized batches of kale juice to determine the length of time needed to kill the melanoma cells.

FIG. 10A depicts a comparison between the time to death of melanoma cells and the batch of the unfiltered juiced kale.

Figure 10B:
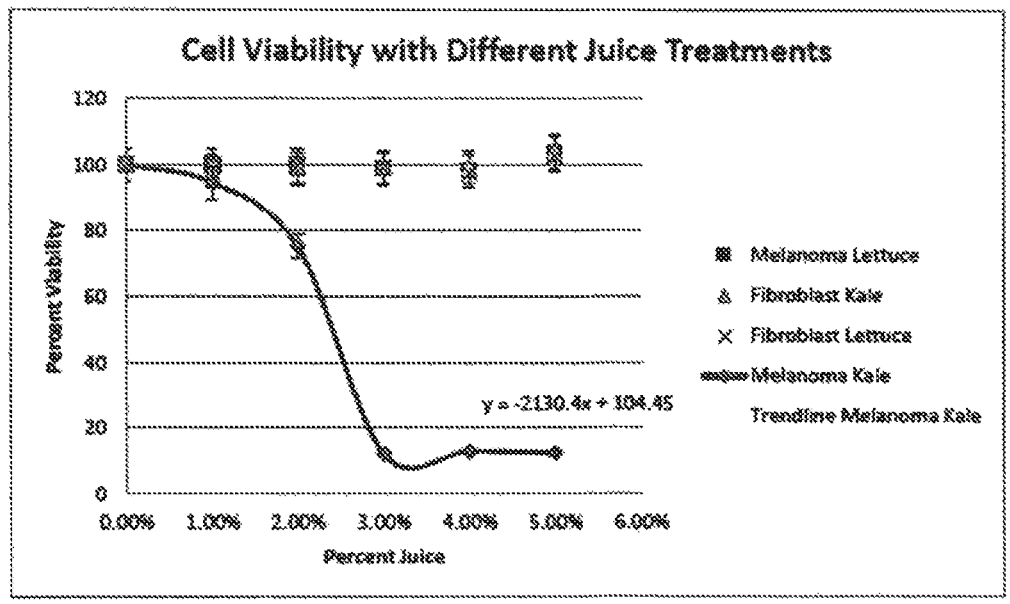
FIG. 10B is a chart reflecting a comparison of the LD50 for a the juiced kale.

FIG. 10B depicts a chart comparing the LD50 of different forms of processed kale. Synchronized melanoma and fibroblast cells were treated with kale and green leaf lettuce juices that were normalized to chlorophyll A content. Solutions were made from juice and cell culture medium. Cells were treated with the respective juices for 24 hours. MTT was used to assess the cell viability. The scatter plot represents the mean of three independent experiments. Error bars represent the standard error of the mean. The LD50 was determined by interpolation using the line of best fit. LD50 for the kale juice treated melanoma cells was at 2.56% kale juice.

Figure 11L:
FIGS. 11A-11J are progressive photographic images of unfiltered juice kale applied to melanoma cells and epithelial cells over a period of 15 hours.
Figure 11J:
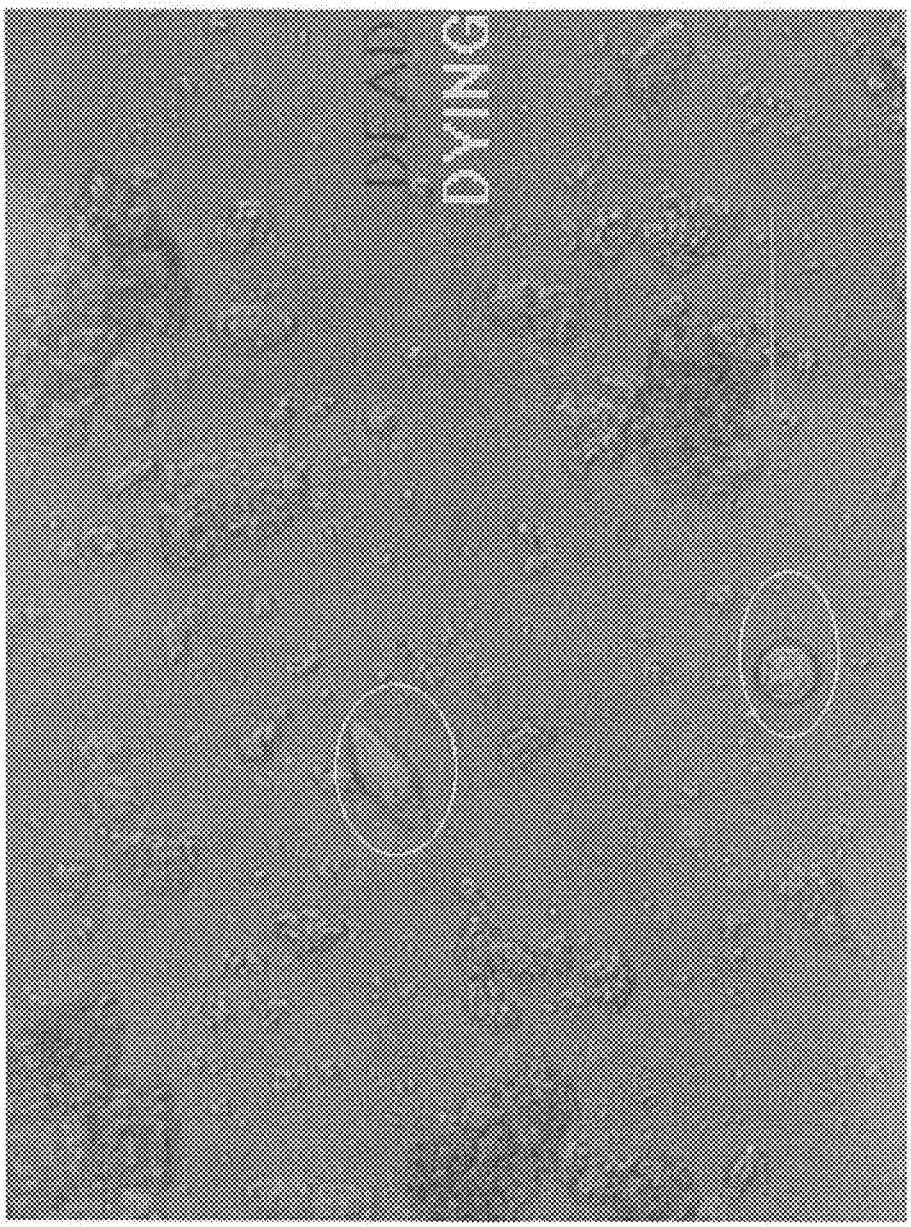

FIGS. 11A-11J are progressive photographic images of unfiltered juice kale applied to melanoma cells and epithelial cells over a period of 15 hours. As shown in FIGS. 11A and 11I (just a magnified version of FIG. 11A), the field of vision included a plurality of viable melanoma cells, juiced kale and a bunch of healthy epithelial cells. However, 15 hours after application, as shown in FIG. 11J, the field of vision included a significant increase in healthy epithelial cells, smaller amounts of juiced kale, and all of the previously viable melanoma cells were either dead or in the processing of dying. It is envisioned, without intent to be limited to, that in embodiments, the success of the juiced kale, as compared to whole kale leaf and/or large pieces of chopped kale leaf, may be based on the ability of the juiced kale to be easily combined with either the melanoma cells and/or the healthy epithelial cells. It is further envisioned, without intent to be limited to, that the proliferation of the healthy cells when exposed to juiced kale further enhances the ability of the epithelial cells to fight against the proliferation of the melanoma cells.

Example 11

NCTC-1469 mouse epithelial cells were grown in Dulbecco's modified Eagle's medium (DMEM)/F12 medium with 10% FBS at 37° C. with 5% $CO_2$. The cell line was purchased from the American Type Culture Collection.

The NCTC-1469 mouse epithelial cells from Example 13 were plated in 24-well plates (200,000 cells/well) in 500 μL of DMEM F12 medium with 0.5% FBS for synchronization. On day two, 47.5 μL FBS was added to each well to bring up the serum concentration of the medium to 10%. The treatments including each of the juiced kales described above were added at a concentration of 7 μL juice/mL/day (0.7%). The medium was changed every four days depending on the duration of the experiment. Cells were inspected each day. Cells were collected for counting as before with the following exceptions: cells were first washed with DMEM F12 w/o FBS and then trypsinized for 4 minutes. Each experiment was repeated at least three times.

Figure 12A:
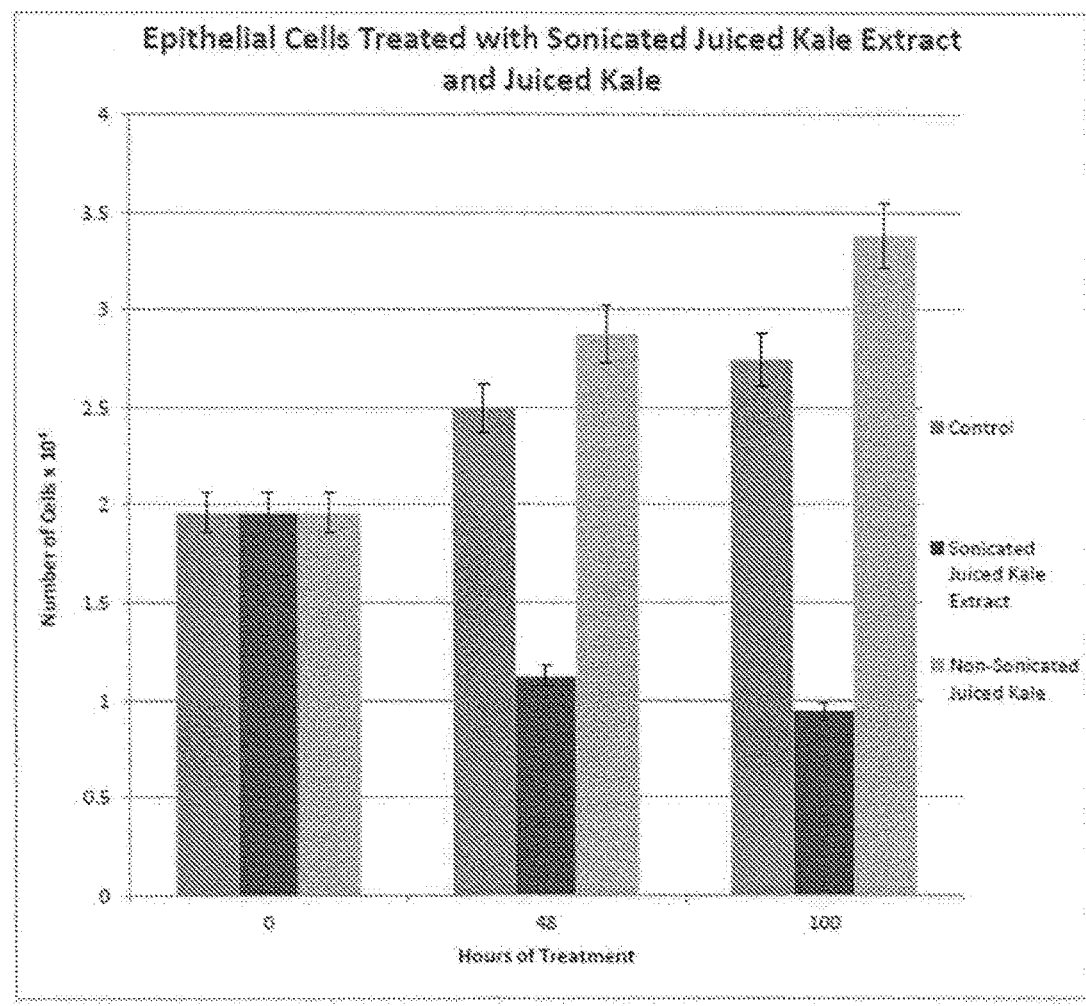
FIG. 12A is a bar graph reflecting a comparison of the ability of unfiltered juiced kale, sonicated kale juice, and a control group to promote epithelial cells.
Figures 13A, 13B, 13C, 13D:
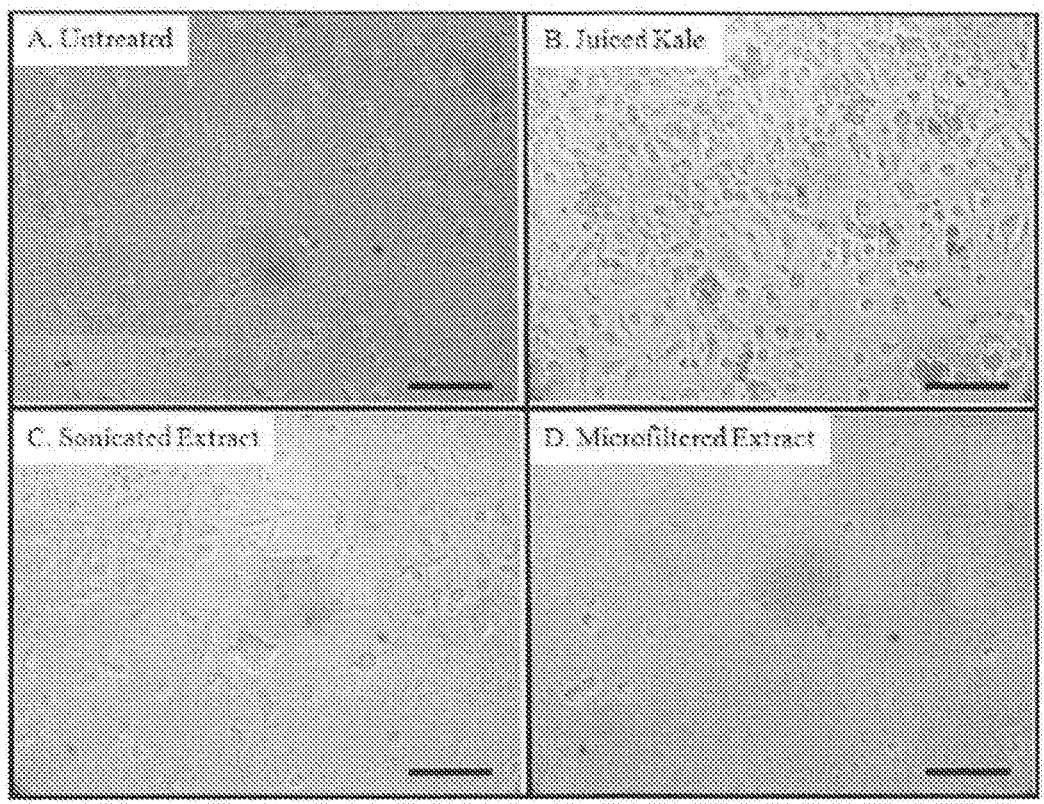
FIGS. 13A-13D are photographic images of untreated epithelial cells and epithelial cells treated unfiltered juiced kale, sonicated juiced kale, and sterile microfiltered kale juice.

FIG. 12A depicts a comparison between unfiltered kale juice (non-sonicated), sonicated kale juice, and a control which reveals that unfiltered kale juice (non-sonicated) not only was non-toxic to the epithelial cells but also promoted the growth of the epithelial cells over 100 hours. Synchronized NCTC-1469 cells were treated with 0.7% of either sonicated juiced kale extract or juiced kale. FIG. 12A shows a graph of mean cell numbers at hours 0, 48 and 100 of the experiment. Graphs represent the mean of three independent experiments. (ANOVA at 100 hour df=2, F=44.7, p=0.001. Student T-test: Untreated v. Sonicated juiced kale extract p=0.0003. Untreated v. Juiced kale p=0.068 Error bars represent the standard error of the mean.)

FIGS. 13A-31D are images at 20× magnification shown untreated and 96 hours after treatment with a 0.7% vol/vol solution of juiced kale (9B), sonicated kale (9C) and Microfiltered. Images were obtained with a Motic inverted microscope equipped with phase contrast at 20×, 96 hours after treatment with a 0.7% vol/vol solution. Scale bar is equal to 100 micrometers.

Example 12

3T3 fibroblast cells were grown in DMEM medium with 10% fetal calf serum (FCS) with 5% $CO_2$. The cell line was purchased from the American Type Culture Collection.

Figures 14A, 14B, 14C:
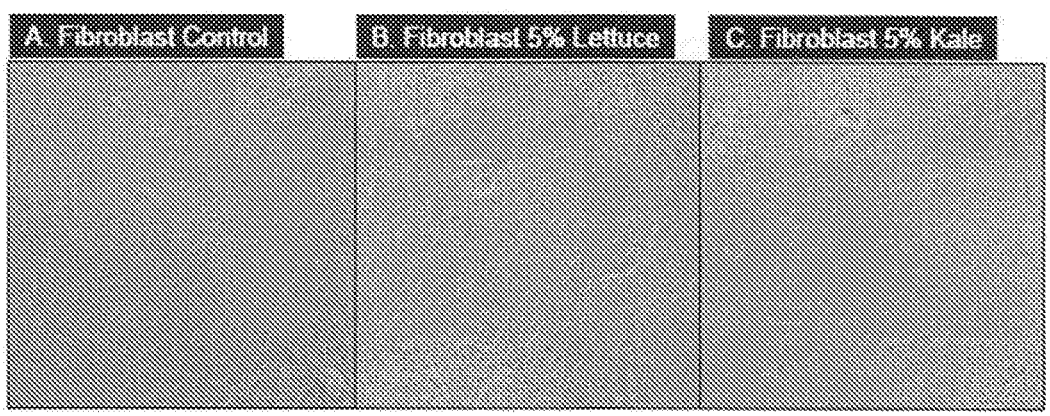
FIGS. 14A-14C are photographic images of untreated fibroblasts and fibroblasts treated unfiltered juiced kale and lettuce juice.
Figure 16A:
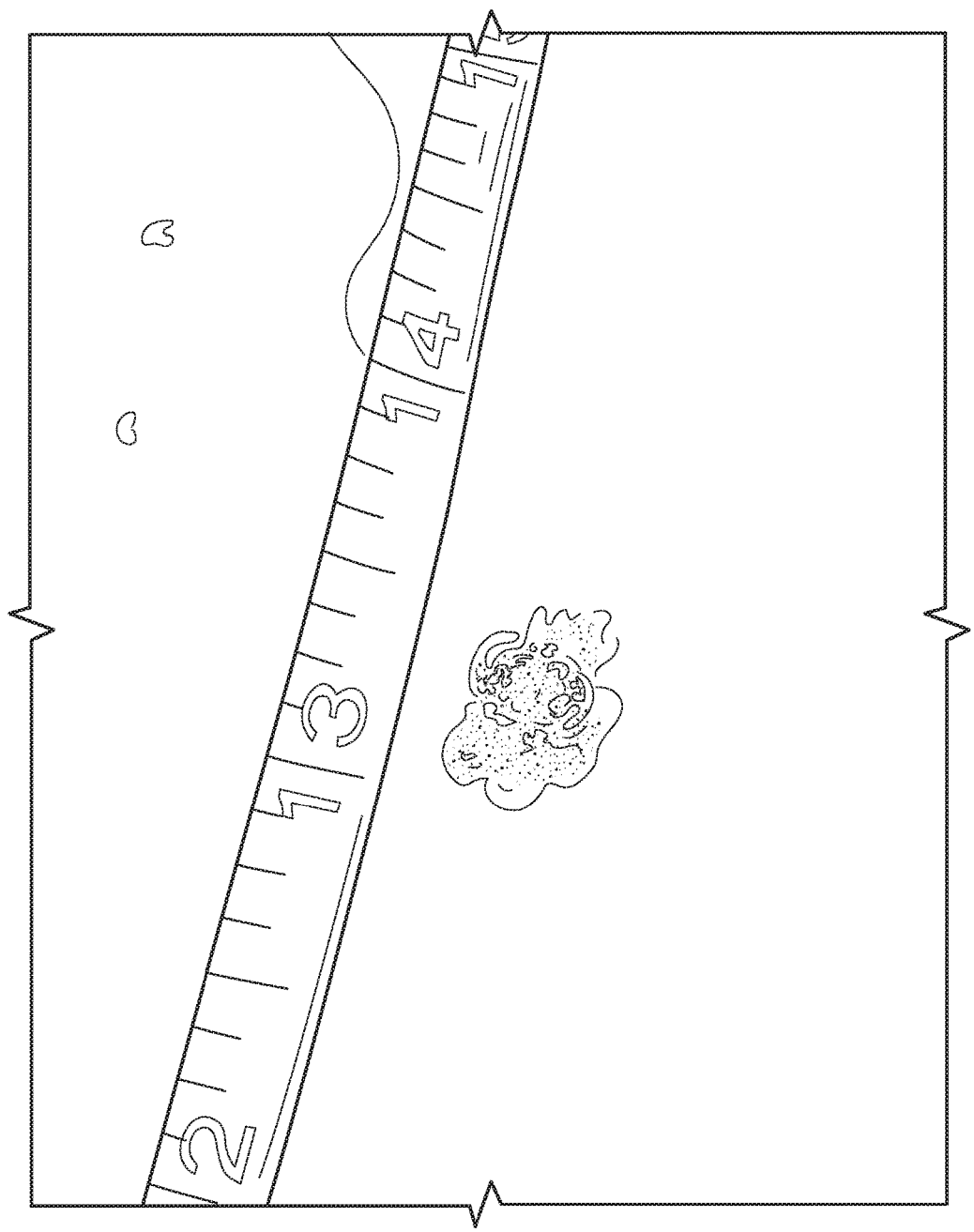
FIGS. 16A-16D are progressive photographic images of a portion of an individual's back, taken at quarterly intervals over an 18-month period, the images illustrating a reduction of a basal cell carcinoma lesion on the portion of the individual's back, the individual having ingested a daily regimen of juiced kale throughout the 18-month period.
Figure 16B:
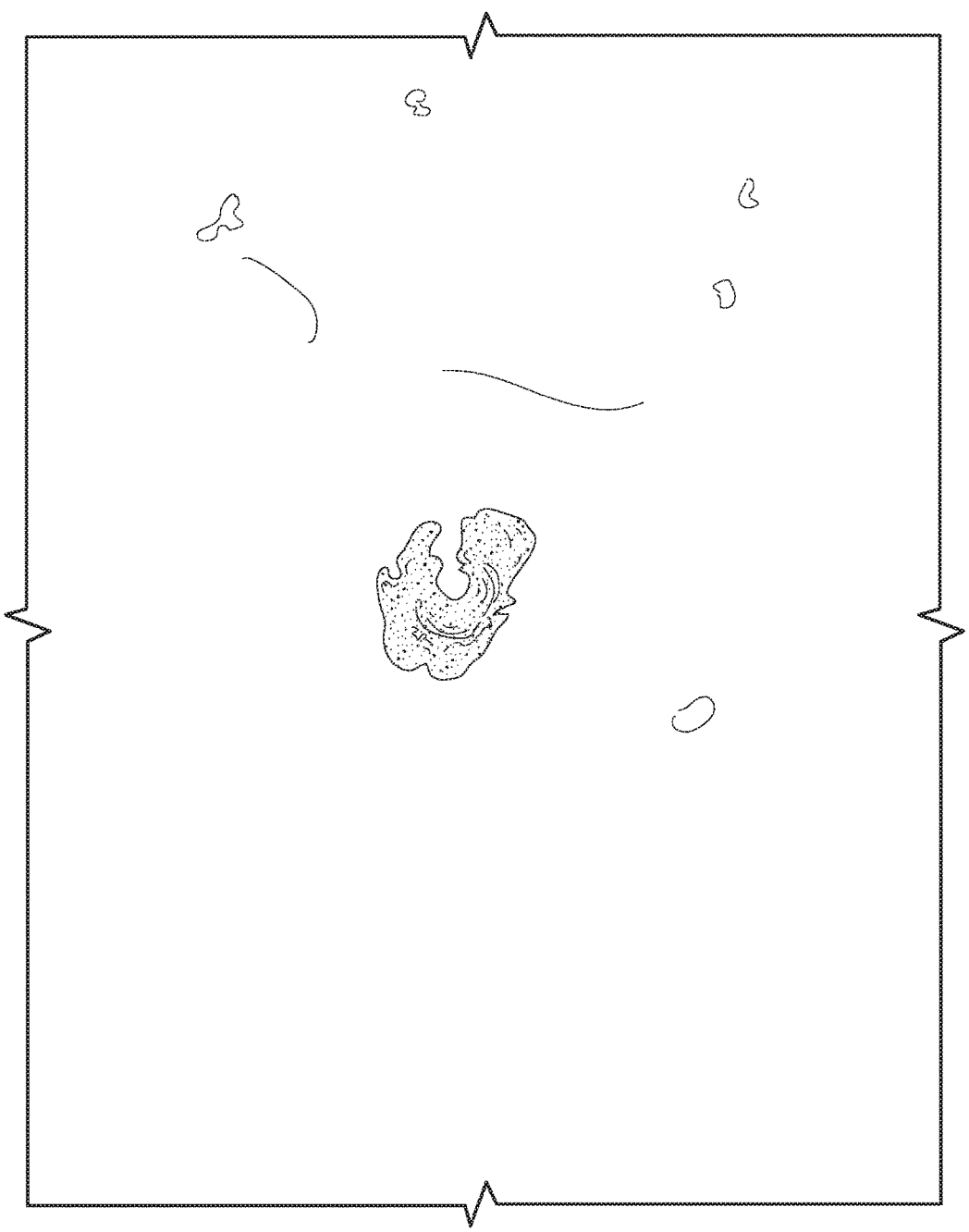
Figure 16C:
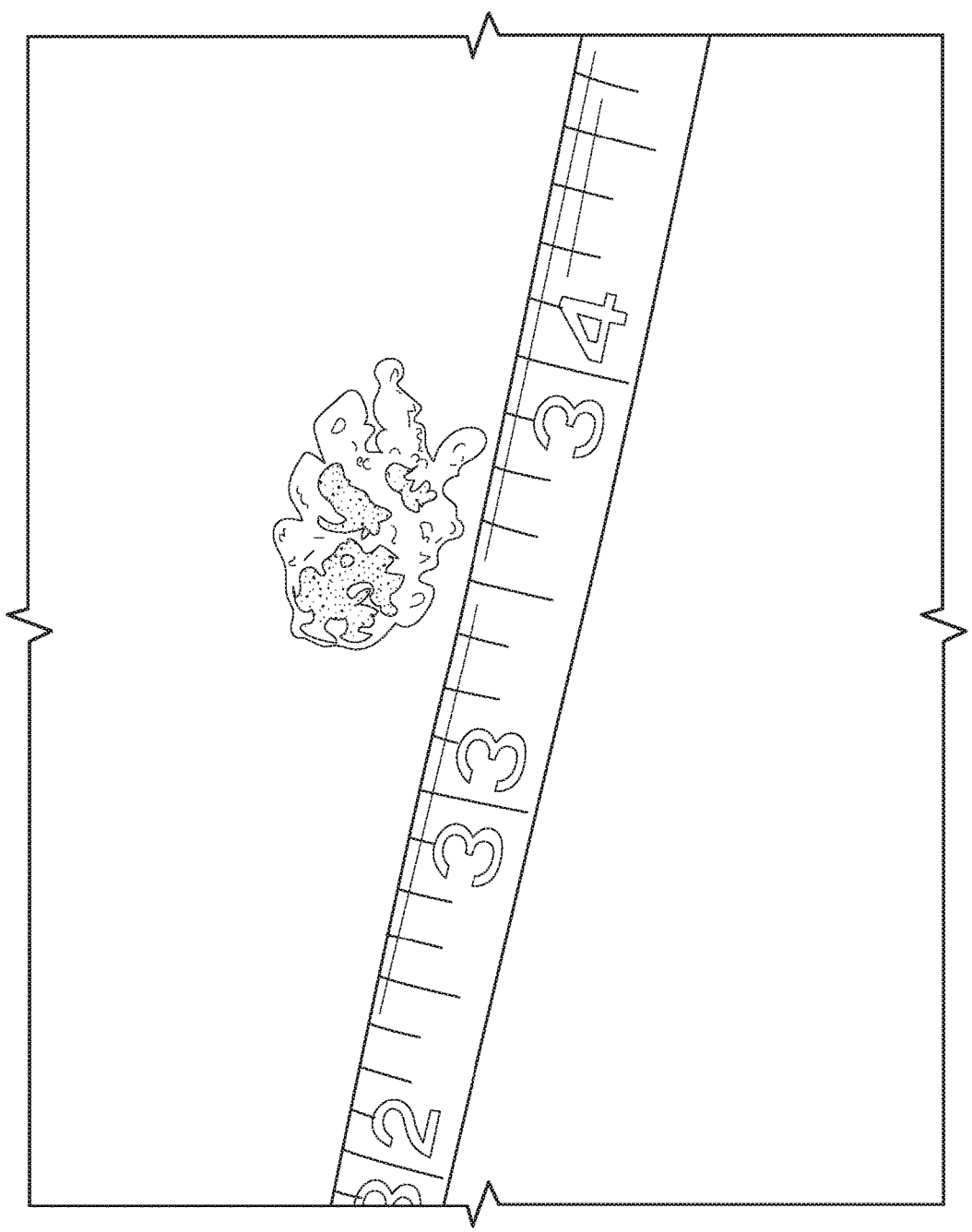
Figure 16D:
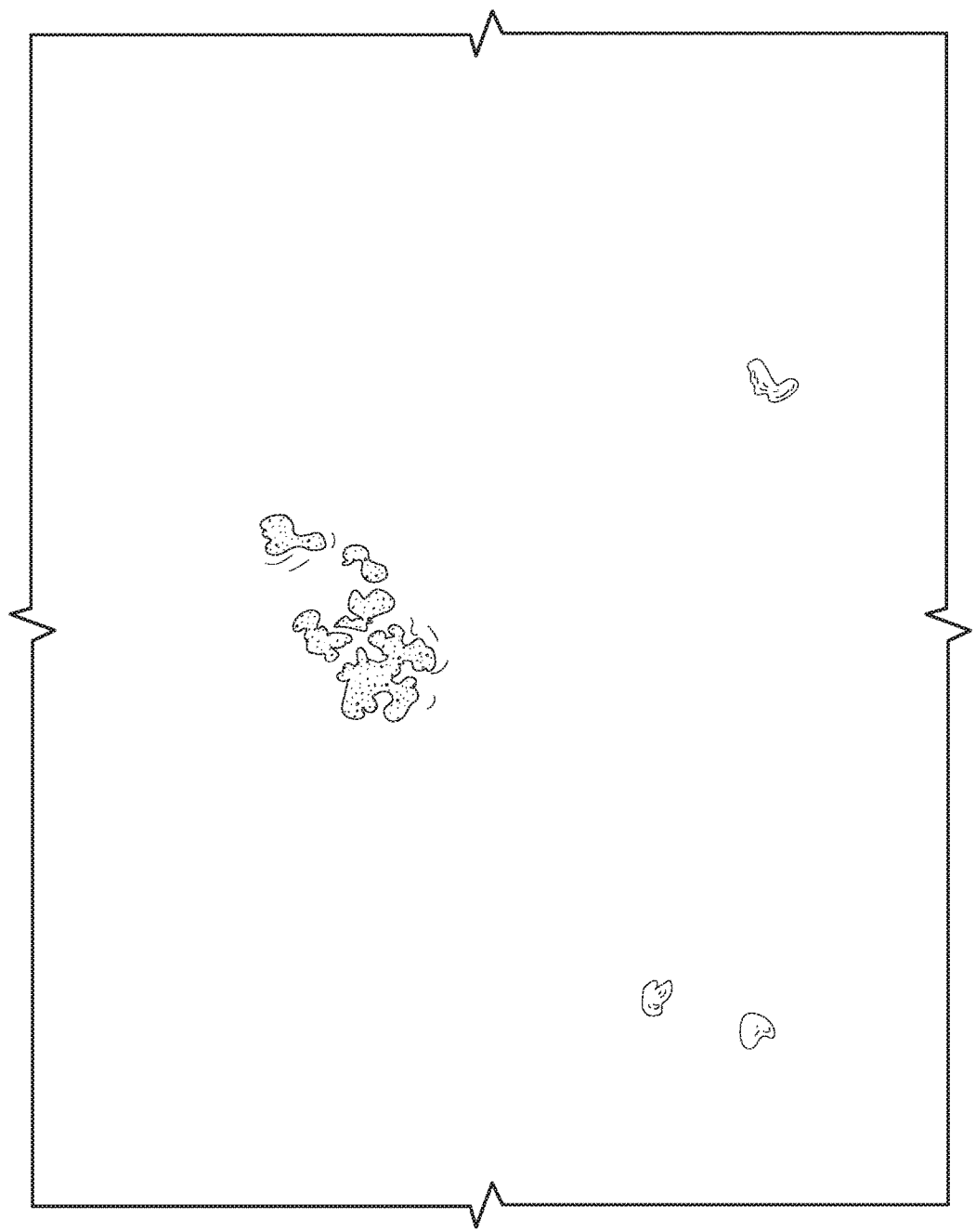

The fibroblasts were treated with 5% lettuce juice or 5% kale. The results are compared in FIGS. 14A-14C. FIGS. 14A-14C show phase contrast images obtained on a Nikon Inverted Eclipse Ti-E microscope with a Nikon DS-Fi2 color camera. Scale bar=100 µm.

FIG. 15 is a table which shows the comparison between the juice treatments, the cancerous cells, and the non-cancerous cells. A summary of the effects of various juice treatments on cultured mouse cells is depicted.

Example 13

A Western blot was performed to check for apoptosis with an anti-PARP antibody (Cell Signaling Technologies). To prepare the samples, 200,000 B16F10 cells were seeded in 12-well plates in 2 mL control medium. The cells were incubated for 24 hours prior to the addition of kale juice. 100 µL of juice was added to the appropriate flask. Cells were incubated for 24 hours and then collected by wash with phosphate buffered saline (PBS). Cells were centrifuged at 1,000×g for 10 min. The supernatant was discarded and the cell pellet was resuspended with RIPA buffer (50 mM Tris-HCl pH8, 1% NP-40, 0.5% DOC, 0.1% SDS, 150 mM NaCl) with protease and phosphatase inhibitors (Sigma). The cells were sonicated with three 15-second bursts at 40%, then centrifuged at 10,000×g for 10 min. The supernatant was saved and a BCA protein assay was performed. 60 µg of samples were subjected to SDS-PAGE on a 4 to 20% Tris-HCl gradient gel and then transferred to PVDF, blotted with rabbit α-poly-ADP ribose polymerase (α-PARP) (Cell Signaling Technologies) and mouse α-tubulin (Sigma). Horse-radish peroxidase conjugated secondary antibodies were produced in goat (Jackson Immunoresearch). Pierce Super Signal Westpico substrate was used for detection. Images were obtained in a Bio-Rad Gel-doc system.

Example 14

A human subject having basal cell carcinomas on his back and skin tags on his eyelid began orally-ingesting a daily regimen of unfiltered juiced kale as described herein over an 18-month period of time. The basal cell carcinomas are depicted in FIGS. 16A-16D, which are progressive photographic images of a portion of the subject's back, taken at quarterly intervals over a year-long period, the images illustrating a reduction of a basal cell carcinoma lesion on the portion of the individual's back, the individual having orally ingested a daily regimen of juiced kale throughout the year-long period.

Figure 17:
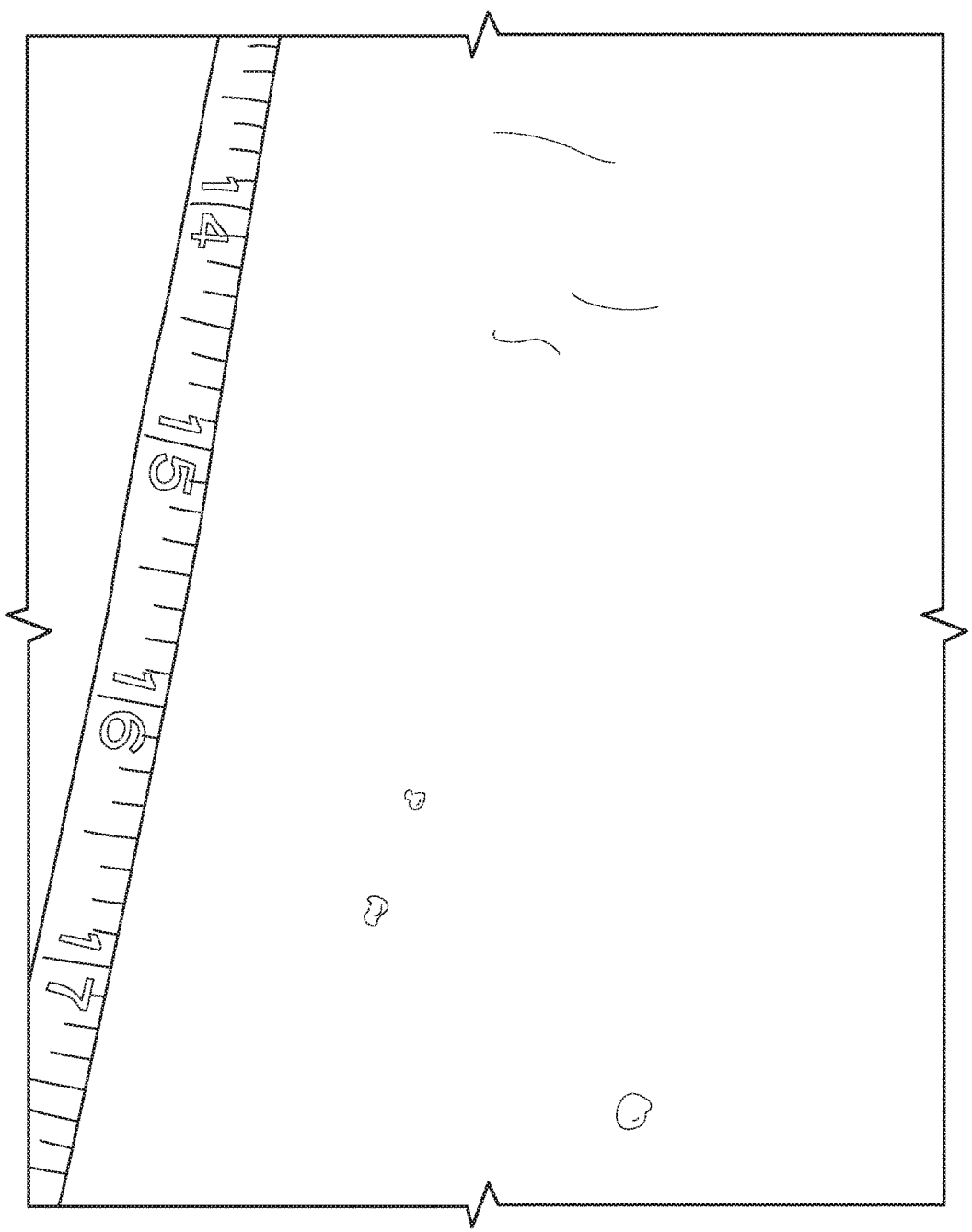
FIG. 17 is a photographic image of the portion of the individual's back taken approximately 18-months after starting the daily regimen of juiced kale.

FIG. 17 is a photographic image of the portion of the individual's back taken approximately 18-months after starting the daily regimen of juiced kale. As can be seen, the basal cell carcinoma has disappeared.

Figure 18:
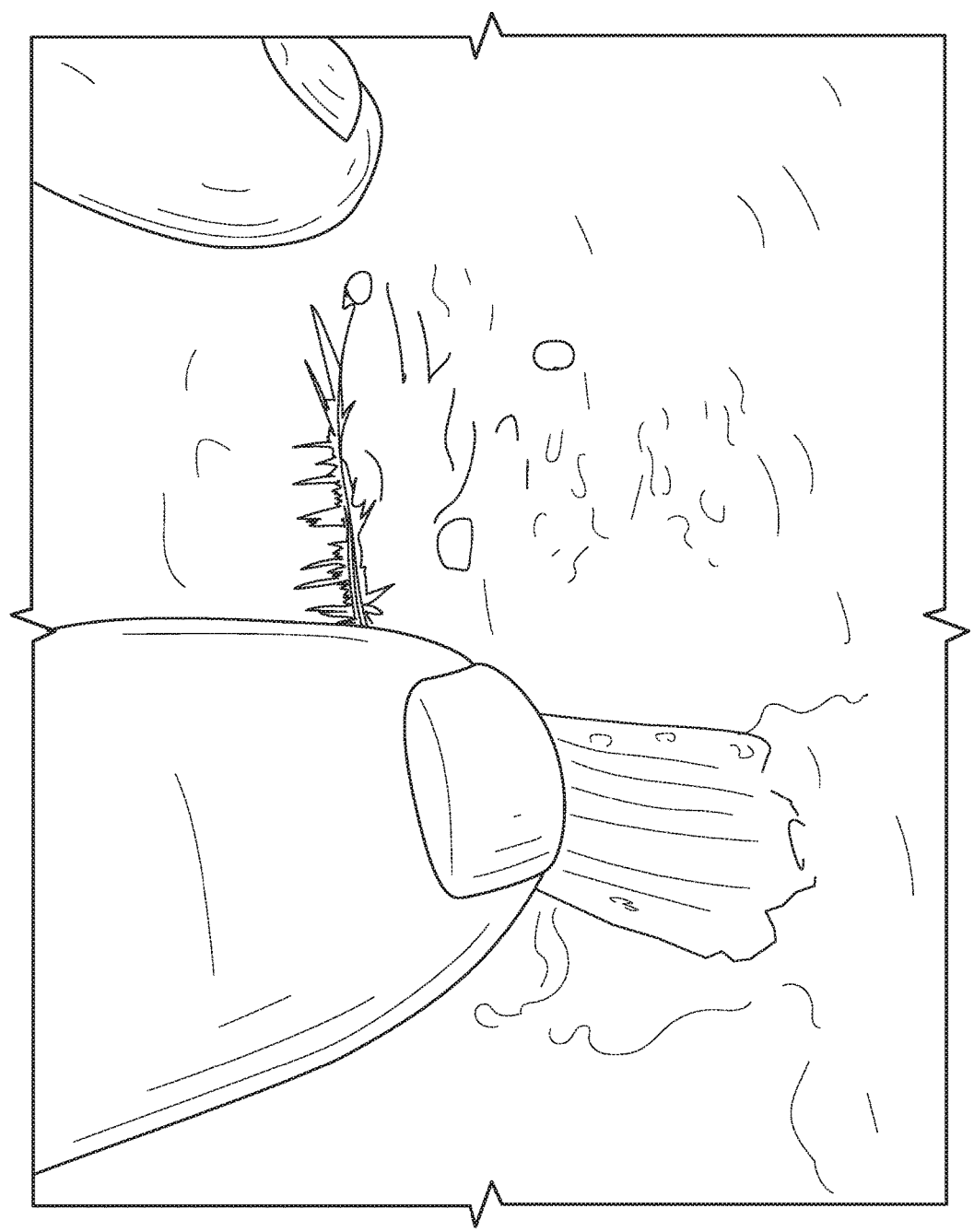
FIG. 18 is a photographic image of the individual's eyelid taken on the first day of the 18-month period.

FIG. 18 is a photographic image of the individual's eyelid taken on the first day of the year-long period.

Figure 19:
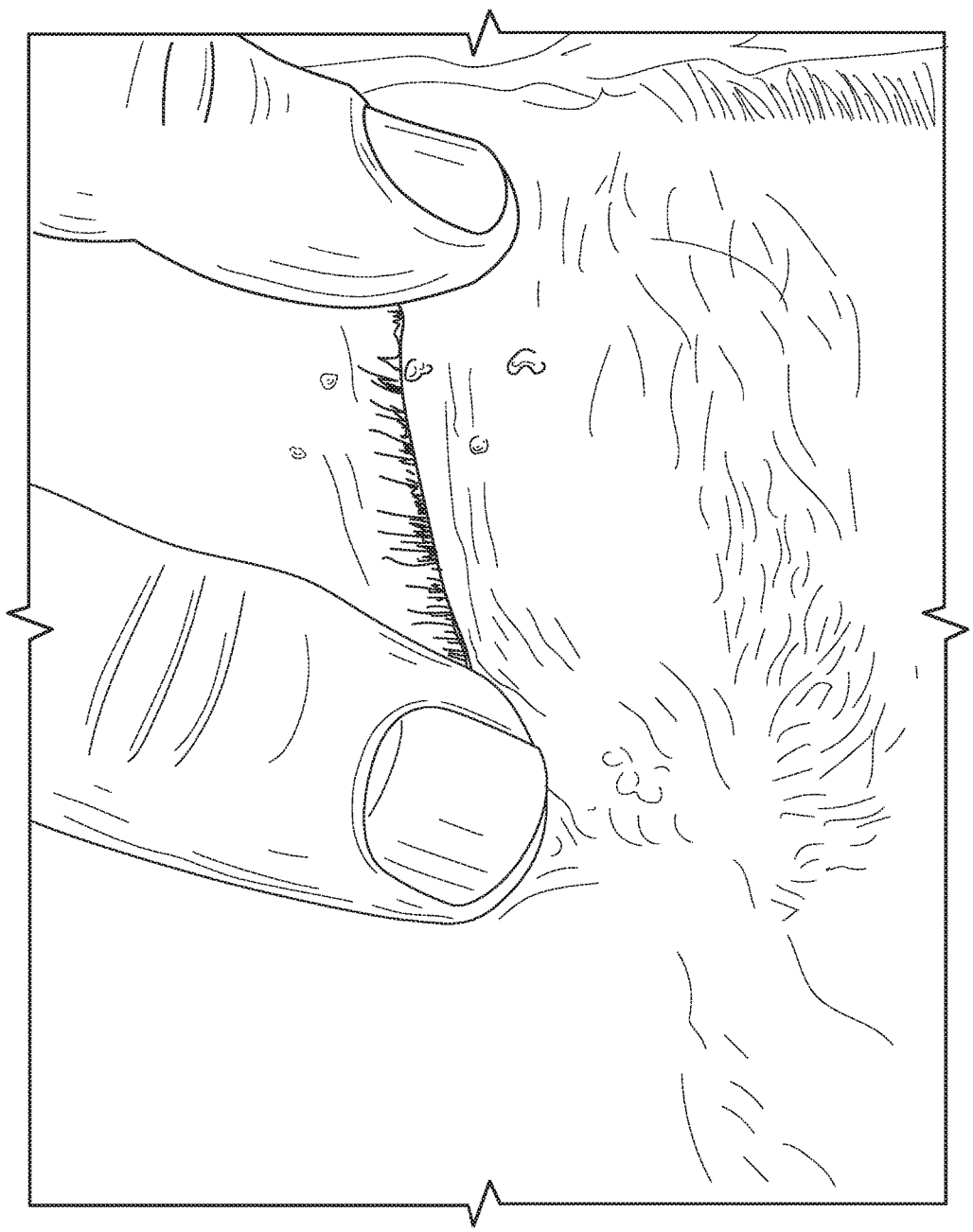
FIG. 19 is a photographic image of the individual's eyelid taken approximately 18-months after starting the daily regimen of juiced kale.

FIG. 19 is a photographic image of the individual's eyelid taken approximately 18-months after starting the daily regimen of juiced kale.

What is claimed is:

1. A method of inducing apoptosis in melanoma cells comprising:
    applying a chemopreventative composition comprising freeze thawed kale juice to melanoma cells.
2. The method of claim 1, wherein the kale of the chemopreventative composition is selected from the group consisting of curly kale, baby kale, organic kale, kale harvested during seeding time, and combinations thereof.
3. The method of claim 2, wherein the kale of the chemopreventative composition comprises curly kale.
4. The method of claim 1, wherein the kale juice of the chemopreventative composition is unfiltered.
5. The method of claim 1, wherein the kale juice of the chemopreventative composition comprises non-heated kale.
6. The method of claim 1, wherein the step of applying the chemopreventative composition includes topical delivery of the composition.
7. The method of claim 6, further comprising applying the chemopreventative composition to non-cancerous cells, wherein the chemopreventative composition is non-toxic to the non-cancerous cells.
8. The method of claim 7, wherein the chemopreventative composition promotes the growth of the non-cancerous cells.
9. The method of claim 8, wherein the non-cancerous cells are epithelial cells.
10. The method of claim 1, further comprising maintaining interaction between the chemopreventative composition and the melanoma cells for more than 7 hours.
11. The method of claim 1, further comprising maintaining interaction between the chemopreventative composition and the melanoma cells for more than 20 hours.
12. The method of claim 1, wherein the chemopreventative composition further comprises at least one of a pharmaceutically acceptable carrier or a surfactant.
13. A method of reducing cancerous or precancerous skin lesions comprising:
    orally-ingesting a chemopreventative composition comprising a juiced kale solution and repeating the step of orally-ingesting the chemopreventative composition on at least a daily basis for at least one week.
14. The method of claim 13, wherein the skin lesion is selected from the group consisting of melanoma, basal cell carcinoma, and skin tags.

* * * * *